United States Patent [19]

Pomidor

[11] Patent Number: 4,885,027

[45] Date of Patent: Dec. 5, 1989

[54] HERBICIDAL ARYLMETHYLENESULFONAMIDO-ACETAMIDE AND THIOACETAMIDE DERIVATIVES

[75] Inventor: Patricia B. Pomidor, Fremont, Calif.

[73] Assignee: Chevron Research Company, San Francisco, Calif.

[21] Appl. No.: 931,278

[22] Filed: Nov. 14, 1986

Related U.S. Application Data

[63] Continuation-in-part of Ser. No. 720,234, Apr. 5, 1985, abandoned, and Ser. No. 774,685, Sep. 11, 1985, abandoned.

[51] Int. Cl.⁴ .................. A01N 41/06; A01N 43/20; C07C 143/78
[52] U.S. Cl. ........................... 71/103; 71/88; 549/553; 558/390; 560/12; 560/13; 562/430; 562/623; 564/74; 564/87; 564/89; 564/94
[58] Field of Search ............ 564/74, 87, 89, 94; 562/430; 560/12, 13; 558/390; 549/553; 71/103, 88; 260/500.5 H

[56] References Cited

U.S. PATENT DOCUMENTS

| Re. 30,837 | 12/1981 | Szmuszkovicz | 514/599 |
|---|---|---|---|
| 2,885,435 | 5/1959 | Pursglove | 564/94 |
| 3,725,452 | 4/1973 | Rumanowski | 564/74 |
| 3,927,002 | 12/1975 | Lombardino | 560/13 |
| 4,113,463 | 9/1978 | Oshio et al. | 560/13 |
| 4,165,258 | 8/1979 | Pye et al. | 564/94 |
| 4,169,719 | 10/1979 | Levitt | 71/92 |
| 4,191,553 | 3/1980 | Reap | 522/211 |
| 4,468,245 | 8/1984 | Takematou et al. | 71/88 |
| 4,544,669 | 10/1985 | LaHann et al. | 514/599 |

FOREIGN PATENT DOCUMENTS

| 68968 | 1/1983 | European Pat. Off. | 562/430 |
|---|---|---|---|
| 97072 | 12/1983 | European Pat. Off. | 564/162 |
| 1101408 | 3/1961 | Fed. Rep. of Germany | 564/94 |
| 2022694 | 6/1975 | Fed. Rep. of Germany . | |
| 2143174 | 1/1976 | Fed. Rep. of Germany . | |
| 2431734 | 1/1976 | Fed. Rep. of Germany . | |
| 2921824 | 12/1979 | Fed. Rep. of Germany | 514/604 |
| 6910209 | 1/1971 | Netherlands | 71/103 |
| 2126586 | 3/1984 | United Kingdom . | |

Primary Examiner—Charles F. Warren
Assistant Examiner—Carolyn S. Greason
Attorney, Agent, or Firm—L. S. Squires; R. C. Gaffney

[57] ABSTRACT

Arylmethylenesulfonamidoacetamide and thioacetamide derivatives and arylmethylenesulfonamidoester intermediates therefor. The compounds are useful as selective herbicides especially with respect to the prevention and elimination of barnyardgrass in grass crops, especially in rice crops.

81 Claims, No Drawings

HERBICIDAL ARYLMETHYLENESULFONAMIDO-ACETAMIDE AND THIOACETAMIDE DERIVATIVES

CROSS-REFERENCE TO RELATED APPLICATIONS

This application is a continuation-in-part of U.S. application Ser. No. 720,234, filed Apr. 5, 1985 and U.S. application Ser. No. 774,685, filed Sept. 11, 1985, both abandoned, the disclosures of which applications are hereby incorporated by reference to their entirety.

BACKGROUND OF THE INVENTION

This invention relates to arylmethylenesulfonamidoacetamide and thioacetamide derivatives and to the use of such compounds as herbicides and plant growth regulators. In a further aspect the invention relates to intermediate and processes for preparing such compounds.

Where herbicides are used to eliminate weeds from crops the herbicide must be effective against the target weed at the application rate used yet safe with respect to the crop. In the case where both the crop and weed species are grasses, it is very difficult to chemically eliminate the grassy weeds without injuring the crop. This is particularly the situation in the case of barnyardgrasses in rice crops.

U.S. Pat. No. 4,191,553 discloses certain arylsulfonamidoamidoheterocycle (Col. 1 lines 29–46) and aryloxysulfonamidocarboxamidoheterocycle herbicides. U.S. Pat. No. 4,169,719 discloses arylsulfonamidocarboxamidoheterocycle herbicides. U.S. Pat. No. 4,468,245 discloses N-(2,3-epoxypropylene)-N-araalkyl sulfonamide herbicides reported to have less phytotoxicity against rice.

West German patent application DE 2,431,734 discloses benzylsulfonamidoacetic acid; benzylbenzylsulfonamidoacetamide; and ethyl (N-methyl-benzylsulfonamido)acetate as intermediates for immunosuppressant. West German patent application DE 2,022,694 discloses N,N-dimethyl-(2-carboxybenzylsulfonamido)acetamide and 2-cyanobenzylsulfonamido)acetamide as intermediates for antispasmodics and narcotics to photosensitive protecting groups. British Pat. No. 2,126,586 discloses certain herbicidal sulfonylureas as giving complete kill of barnyardgrass without damage to rice.

European patent application No. 68968 discloses a genus of compounds having the formula:

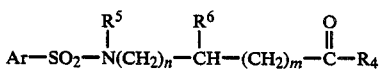

wherein Ar is optionally substituted aryl; $m+m+1=3-11$ and $R_4$ is hydroxy, alkoxy or $-NR_8R_9$ wherein $R_8$ and $R_9$ are especially hydrogen or together with the nitrogen atom forms heterocycle. $R_5$ and $R_6$ are especially alkyl. The compounds are described as being useful as normolipaemics (i.e., antilipids).

U.S. Pat. No. 2,885,435 discloses a genus of compounds having the formula:

wherein R is alkyl, aryl, haloaryl, nitroaryl and G is $-C(O)-$ or $-SO_2-$.

Patentee broadly teaches that among other useful characteristics, patentee's compounds frequently have biochemical value as either fungicides, herbicides, insecticides, nematocides, or the like, depending upon their individual properties and capabilities. The only specific activity disclosed was the control of the organisms *Salmonella typhosa* and Staphylococus in agar cultures.

SUMMARY OF THE INVENTION

The present invention provides compounds having excellent selective pre-emergence and post-emergence herbicidal activity against barnyardgrass. In addition, the present compounds exhibit excellent safety with respect to both broadleaf and grassy crops, including rice.

The compounds of the present invention can be represented by the following formulas:

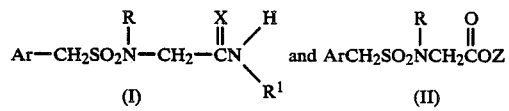

wherein
R is hydrogen, lower alkyl having 1 through 6, preferably 1 through 4, carbon atoms; cycloalkyl having 3 through 6 carbon atoms; (cycloalkyl)alkyl wherein the cycloalkyl moiety has 3 through 6 carbon atoms and said alkyl moiety has 1 through 3 carbon atoms, preferably 1 or 2; lower alkenyl having 2 through 6, preferably 2 through 4, carbon atoms; lower alkynyl having 2 through 6 carbon atoms; 3-iodopropargyl; alkanoyl having 2 through 6 carbon atoms, preferably 2 through 4 carbon atoms, alkoxyalkyl wherein the alkoxy and alkyl moieties independently have 1 through 6, preferably 1 through 4 carbon atoms; alkylthioalkyl wherein the alkyl moieties independently have 1 through 6, preferably 1 through 4, carbon atoms; epoxyalkylmethyl having the formula R'—CH$_2$— wherein R' is epoxyalkyl having 1 through 5 carbon atoms; cyanomethyl; or haloalkylmethyl having 2 through 4 carbon atoms and 1 through 4 halo atoms independently selected from the group of fluoro, chloro and bromo;

X is oxo(O=) or thioxo (S=);

$R^1$ is hydrogen, hydroxy or alkanoyl having 2 through 5 carbon atoms with the proviso that when X is thioxo, then $R^1$ is hydrogen;

Ar is a substituted phenyl selected from the group of tetrafluorophenyl; pentafluorophenyl; trisubstituted phenyls having three substituents independently selected from the group of fluoro, chloro, bromo or trifluoromethyl; or a substituted phenyl having the formula

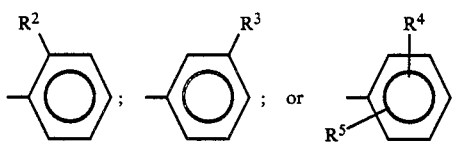

wherein $R^2$ is methyl, trifluoromethyl or chloro;

$R^3$ is halo, alkyl having 1 through 4 carbon atoms, alkoxy having 1 through 4 carbon atoms, fluoroalkyl having 1 through 4 fluoro atoms and 1 through 4 carbon atoms (preferably trifluoromethyl) or nitro; one of $R^4$ or $R^5$ is trifluoromethyl or chloro and the other is halo, nitro, alkyl having 1 through 4 carbon atoms, alkoxy having 1 through 4 carbon atoms, or fluoroalkyl having 1 through 4 fluoro atoms and 1 through 4 carbon atoms; and Z is lower alkyl having 1 through 6, preferably 1 through 4, carbon atoms; phenyl; benzyl; or naphthyl.

The invention also includes hydrates and compatible salts of the compounds of Formula (I). Such salts are generally cation salts formed with respect to the nitrogen atom of the terminal amide group.

In the case where the R substituent creates an asymmetric carbon atom the compounds can also exist as optical isomers. Also depending on the particular substituent, in some instances the compounds also exist as geometric isomers. The above formula is intended to encompass the respective individual isomers as well as mixtures thereof and the respective isomers as well as mixtures thereof are encompassed within the invention.

The compounds of Formula (I) wherein R is hydrogen are only weakly active or wholly inactive as herbicides but, are useful as intermediates to prepare various R substituted analogs which exhibit excellent selective herbicidal activity against barnyardgrass. The R is hydroxyalkylmethyl also generally have poor herbicidal activity but are useful as intermediates for the R is haloalkylmethyl compounds via conventional halide replacement. Similarly, the compounds of Formula (II) are intermediates for the compounds of Formula (I).

In a still further aspect the invention provides a herbicidal composition comprising a compatible carrier and a herbicidally effective amount of the active compound(s) of the invention or mixtures thereof.

The present invention also provides a method for preventing or controlling the growth of unwanted vegetation, which comprises treating the growth medium and/or the foliage of such vegetation with a herbicidally effective amount of the active compound(s) of the invention or mixtures thereof.

In another aspect, the present invention provides a plant growth regulating composition comprising a compatible carrier and a plant growth regulating amount of the active compound(s) of the invention or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of the invention or mixtures thereof, effective to alter the normal growth pattern of said plants.

The present invention also provides chemical intermediates and processes for preparing the herbicidal compounds of the invention.

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 2, 3, 4 and 7-13 set forth hereinbelow on pages 28 to 36 and 37 to 55. Illustrations of typical compounds of Formula (II) can be had by reference to Example 1, pages 27 to 28.

In terms of substituents and herbicidal activity, the preferred compounds are those wherein R is lower alkyl having 1 through 4 carbon atoms, lower alkenyl, lower alkynyl, 3-iodopropargyl, fluoroalkylmethyl, cycloalkyl, (cyclopropyl)methyl and methoxymethyl. Especially preferred R-groups are methyl, ethyl, 2-propynyl, 2-fluoroethyl, 2,2,2-trifluoroethyl, cyclopropyl and methoxymethyl. $R^1$ is preferably H. Ar is preferably pentafluorophenyl, or monosubstituted phenyl, more preferably having its single substituent at the 3-position. Especially, preferred Ar-groups are the groups 3-trifluoromethylphenyl, and 3-chlorophenyl. In the case of disubstituted Ar groups, the Ar groups 3,5-dichlorophenyl, 2-chloro-5-trifluoromethylphenyl and 3,5-ditrifluoromethylphenyl are preferred. In the case of trisubstituted Ar groups, the Ar groups 2,3-dichloro-5-trifluoromethylphenyl and (2,3,6-trichlorophenyl) are preferred. Generally, the X is oxo compounds exhibit superior herbicide activity to the X is thioxo compounds and hence are preferred. Also, the mono- and disubstituted Ar-groups are preferred to the trisubstituted Ar-group. With respect to intermediate II, Z is preferably a simple methyl or ethyl group.

Most preferably the compounds contain a combination of two or more preferred Ar, R, substituents.

Examples of specific compounds which exhibit excellent selective herbicidal activity against barnyardgrass, include:

(N-ethyl-3-trifluoromethylbenzylsulfonamido)acetamide;

(N-allyl-3-trifluoromethylbenzylsulfonamido)acetamide;

(N-2'-propynyl-3-trifluoromethyllbenzylsulfonamido)acetamide;

(N-2'-fluoroethyl-3-trifluoromethylbenzylsulfonamido)acetamide;

(N-2',2',2'-trifluoroethyl-3-trifluoromethylbenzylsulfonamido)acetamide;

(N-cyclopropyl-3-trifluoromethylbenzylsulfonamido)acetamide;

(N-methoxymethyl-3-trifluoromethylbenzylsulfonamido)acetamide;

(N-ethyl-3-chlorobenzylsulfonamido)acetamide;

(N-ethyl-3,5-dichlorobenzylsulfonamido)acetamide;

(N-ethyl-2-chloro-5-trifluoromethylbenzylsulfonamido)acetamide;

(N-ethyl-pentafluorophenylmethylsulfonamido)acetamide;

(N-ethyl-3,5-di-trifluoromethylbenzylsulfonamido)acetamide; and (N-ethyl-2,3-dichloro-5-trifluoromethylbenzylsulfonamido)acetamide.

The corresponding thioacetamide derivatives of the above compounds also exhibit preferred activity, but generally are less active than the acetamide derivatives.

In developing this class of compounds, we have found that this unique selective activity is sensitive to even minor structural changes at certain positions of the molecule. Thus, the aryl moiety must be separated from the sulfonyl moiety by a methylene bridge. Direct attachment renders the compound inactive and even separation by a branched alkyl group, e.g., 1'-ethyl or 2-propyl destroys or substantially reduces activity.

The compounds of Formula (I) wherein X is oxo and $R^1$ is hydrogen can be prepared via amination of the corresponding carboxy esters of Formula (II):

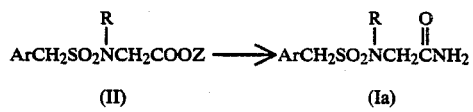

(II) (Ia)

wherein Ar, R, and Z are as defined hereinabove.

This process can be conveniently effected by contacting Compound (II) with ammonium hydroxide, under reactive conditions, in the presence of water, and optionally in an inert organic solvent.

Typically, this process is conducted at temperatures in the range of about from 25° to 100° C., preferably about from 25° to 50° C., for about from 1 to 36 hours, preferably about from 1 to 20 hours, using about from 1 to 200, preferably 1 to 100, moles of ammonium hydroxide per mole of Compound (II).

The starting materials of Formula (II) are novel compounds and can be prepared via the following schematically represented process:

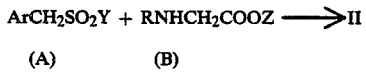

(A) (B)

wherein Ar, R, and Z are as described hereinabove and Y is chloro or bromo.

This process can be conveniently effected by contacting Compound (A) with Compound (B) or an addition salt thereof, under reactive conditions in the presence of base and generally water, and preferably in an inert organic solvent.

Typically, this process is conducted at temperatures in the range of about from 60° to 100° C., preferably about from 70° to 80° C., for about from 2 to 8 hours, preferably about from 4 to 5 hours, using about from 1 to 5, preferably 2 to 3, moles of Compound (B) and 1 to 5 moles, preferably 1 to 3 mole of base, per mole of Compound (A). Suitable bases which can be used include, for example, potassium carbonate, sodium carbonate, and the like. Best results are typically obtained using potassium carbonate. Suitable inert organic solvents which can be used include, for example, 1,2-dichloroethane, methylene chloride, and the like, and compatible mixtures thereof.

The starting materials of Formulas (A) and (B) are known compounds or can be prepared by the adaptation of known procedures using appropriately substituted starting materials. The process is an especially convenient synthesis for the R is hydrogen or methyl compounds because the appropriate R is hydrogen or methyl compounds of Formula (B) are readily commercially available. The arylmethylsulfonyl chlorides of Formula (A) can, for example, be prepared by the following schematically represented process:

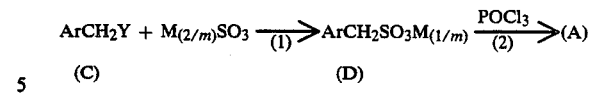

(C) (D)

wherein Y is chloro or bromo; M is a cation and m is its valence; and R is as defined hereinabove.

The first step of this process can be conveniently effected by contacting Compound (C) with a sulfite salt, in water and optionally an inert organic solvent.

Typically, this process is conducted at temperatures in the range of about from 70° to 100° C., preferably 90° to 100° C., for about from 2 to 8 hours, preferably 4 to 5 hours, using about from 1 to 2, preferably 1 to 1.2 mole equivalents of sulfite salt per mole of Compound (C).

Suitable sulfite salts (C) which can be used include, for example, alkali metal sulfites, for example, potassium sulfite; sodium sulfite; ammonium sulfite; and the like. Typically, simple sulfites, such as sodium sulfite, are preferred as they are relatively inexpensive and give good results.

Suitable optional inert organic solvents which can be used include, for example, liquid alkanols, glycols, dimethylformamide and the like, and compatible mixtures thereof.

The starting materials of Formula (C) are generally known materials and can be prepared by known procedures, or obvious modifications thereof (i.e., substitution of appropriate starting materials). For example, many of the starting materials of Formula (C) can be prepared by halogenating the corresponding substituted toluenes by adapting the procedure described in Organic Synthesis, Collective Vol. V, page 825. Compounds such as m-trifluoromethylbenzyl chloride can be conveniently prepared via chloromethylation of the corresponding toluene derivative; e.g. alpha, alpha, alpha-trifluorotoluene.

The second step of this process can be conveniently effected by contacting Compound (D) with phosphorous oxychloride optionally in a solvent.

Typically, this process is conducted at temperatures in the range of about from 80° to 200° C., preferably 100° to 110° C. for about from 2 to 8 hours, preferably 4 to 5 hours, using about from 1 to 10, preferably 1.5 to 5 moles of phosphorous oxychloride per mole equivalent of Compound (D). If desired excess phosphorous oxychloride can be used as solvent or inert organic solvents such as toluene could also be used.

The compounds of Formula (A) having an ortho and/or para alkyl substituent are typically more conveniently prepared by chlorination of the corresponding alkylbenzylmercaptan by adapting the procedure described in *J. Am. Chem. Soc.,* V. 60, p. 1486 (1938).

In some instances it is preferable to prepare certain of the R-substituted compounds of Formula (I) from the corresponding R-unsubstituted compound of Formula (I). This process can be schematically represented by the overall reaction equation:

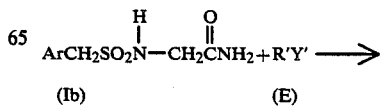

(Ib) (E)

-continued

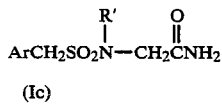
(Ic)

wherein Ar, is as defined hereinabove and R' is as defined for R, hereinabove, but is other than hydrogen; and Y' is bromo or iodo, or R'Y' can be dialkylsulfate.

The above process is a general procedure but is especially useful to prepare the compounds of Formula (I) wherein R is alkyl, alkenyl, alkoxyalkyl, hydroxyalkyl, epoxyalkylmethylene, haloalkylmethylene, cyanomethyl or alkylthioalkyl. This process can be effected as a phase transfer reaction by contacting Compound (Ia) with Compound (E) in water and an inert water immiscible organic solvent in the presence of base and a phase transfer agent.

This process is typically conducted at temperatures in the range of about from 0° to 80° C., preferably, 25° to 80° C., for about from 1 to 36 hours, preferably 2 to 24 hours using about from 1 to 2 moles, preferably 1 to 1.2 mole equivalents of Compound (E) and 1 to 2 mole equivalents, preferably about 1 mole equivalent of base and 0.05 to 1 mole equivalents, preferably 0.05 to 0.3 mole equivalents of phase transfer agent per mole of Compound (Ia).

Suitable inert water immiscible organic solvents which can be used include, for example, chloroalkanes, e.g. methylene chloride, 1,2-dichloroethane, and trichloroethane; toluene, and the like and compatible mixtures thereof. Typically about from 1 to 8, preferably 3.5 to 5.5 liters of inert organic solvent are used per mole of Compound (Ia). Generally, water to immiscible solvent volume ratios of about from 1:3 to 1:20, preferably about 1:10 are used.

Suitable phase transfer agents which can be used are compounds which transfer hydrophilic ions into liquid lipophilic organic mediums and include benzyl triethylammonium chloride, methyl trioctylammonium chloride, tetrabutyl ammonium chloride, tetrabutyl ammonium bromide and the like. Very good results are typically obtained using benzyl triethylammonium chloride as the phase transfer agent.

Suitable bases which can be used include, for example, sodium hydroxide, potassium hydroxide, sodium carbonate, potassium carbonate, lithium carbonate, and the like.

The above process can also be conducted by contacting Compound (Ia) with Compound (E) in the presence of a strong base, such as sodium hydride, preferably in an inert organic solvent. In the case where Compound (E) is a sulfenyl halide the reaction is preferably carried out using a weak base, such as pyridine.

This process is typically conducted at temperatures in the range of about from 0° to 100° C., preferably, 25° to 60° C, for about from 1 to 24 hours, preferably 2 to 4 hours using about from 1 to 2 moles, preferably 1 to 1.1 mole equivalents of the Compound (E) and 1 to 1.2 moles, preferably about 1 to 1.1 mole equivalents of strong base per mole of Compound (Ia).

Suitable strong bases which can be used include, for example, sodium hydride, lithium hydride, potassium hydride, and the like. Suitable inert organic solvents which can be used include for example dimethylformamide, tetrahydrofuran, dimethylsulfoxide, and the like and compatible mixtures thereof.

The compounds of Formula (Ia) can also be prepared from the corresponding arylmethylenesulfonamide derivatives by the following schematically represented process:

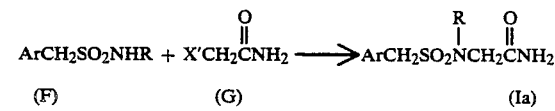

wherein Ar and R are as defined hereinabove and X' is bromo or iodo.

This process is especially useful to prepare the "R is cyclopropyl" compounds of (Ia).

Thes process can be conducted as a phase transfer reaction and can be effected by contacting Compound (F) with bromo- or iodoacetamide (G) in water and an inert water immiscible organic solvent in the presence of base and a phase transfer agent.

This process is typically conducted at temperatures in the range of about from 0° to 80° C., preferably, 25° to 80° C., for about from 1 to 36 hours, preferably 2 to 24 hours using about from 1 to 2 moles, preferably 1 to 1.2 moles of bromo- or iodoacetamide and about 1 to 2 mole equivalents, preferably about 1 to 1.2 mole equivalents of weak base and 0.05 to 1 mole equivalents, preferably 0.5 to 0.3 mole equivalents of phase transfer agent per mole of Compound (F).

Suitable immiscible solvents, bases, and phase transfer agents include those illustrated with respect to the previously described phase transfer reaction.

Thes process can also be effected by contacting Compound (F) with bromo- or iodoacetamide in the presence of base, preferably in an inert organic solvent.

This process is typically conducted at temperatures in the range of about from 0° to 100° C., preferably, 25° to 60° C., for about from 1 to 24 hours, preferably 2 to 4 hours using about from 1 to 2 moles, preferably 1 to 1.1 moles of bromo- or iodoacetamide and 1 to 1.2 mole equivalents, preferably about 1.1 mole equivalents of strong base per mole of Compound (F).

Suitable strong bases which can be used include, for example, lithium hydride, sodium hydride, potassium hydride, and the like. Suitable inert organic solvents which can be used include for example, dimethylformamide, tetrahydrofuran, dimethylsulfoxide, and the like and compatible mixtures thereof.

The starting materials of Formula (F) can be prepared by reacting the corresponding compound of Formula (A), with ammonium hydroxide (R=H) or the corresponding R primary amine (RNH$_2$).

The compounds of Formula (I), which do not have easily acid and base hydrolyzed substituents, can also be prepared by hydrolysis of the corresponding acetonitrile analogs

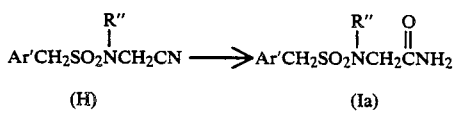

Ar' is as defined for Ar, hereinabove, but does not have easily acid or base hydrolyzed substituents and R" is as defined for R, hereinabove, but is not an easily acid or base hydrolyzed group (e.g., R" is not —CN).

This process can be effected by contacting Compound (H) with an acid or base under reactive conditions generally in the presence of water.

Typically, this process is conducted at temperatures in the range of about from 50° to 100° C., preferably about 70° to 100° C., for about from 5 to 60 minutes, preferably about from 5 to 15 minutes, using about from 1 to 10, preferably 5 to 7, mole equivalents of acid per mole of Compound (H). Suitable acids which can be used include, for example, sulfuric acid; acetic acid and boron trifluoride; formic acid and hydrochloric acid or hydrobromic acid, and the like. Where Compound (H) does not have an acid hydrolyzed substitution good results are typically obtained using concentrated sulfuric acid. Suitable bases which can be used include, for example, strong bases, e.g., sodium hydroxide and potassium hydroxide. Base hydrolysis can be conveniently conducted using a strong base such as potassium hydroxide in the presence of hydrogen peroxide.

The compounds of Formula (H) are described in my copending Application Ser. No. 720,233, filed Apr. 5, 1985, and hereby incorporated by reference in its entirety. These compounds can be prepared by the following schematically represented process:

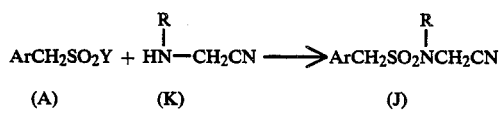

(A)    (K)    (J)

wherein Y is chloro or bromo, preferably chloro, and Ar and R are as defined herein above.

This process can be conveniently effected by contacting Compound (A) with Compound (K) or an addition salt thereof, preferably in the presence of a base, and generally water, preferably in an inert organic solvent.

Typically, this process is conducted at temperatures in the range of about from 0° to 100° C., preferably about from 20° to 80° C., for about from 2 to 8 hours, preferably about from 3 to 5 hours, using about from 1 to 5, preferably 1.5 to 3 moles of Compound (K) per mole of Compound (A). Suitable bases which can be used include, for example, inorganic bases such as for example, potassium carbonate, sodium hydroxide, sodium carbonate, and the like, as well as organic bases such as for example trialkylamine (for example triethylamine) pyridine, and the like. Where an inorganic base is used the process is also conducted in the presence of water and higher reaction temperatures are required. The base serves to scavenge the hydrogen halide formed by the reaction and also when a salt of Compound (K) is used the base serves to liberate Compound (K) for the reaction. Suitable organic solvents which can be used include, for example, methylene chloride, 1,2-dichloroethane, and the like, and compatible mixtures thereof.

Best results are typically obtained using about one and a half equivalents of Compound (K) and about one equivalent of base (e.g., pyridine) per equivalent of Compound (A) and running the reaction in dichloromethane.

As in the case of the acetamides of Formula (Ia), variation in the R substituent of the acetonitriles of Formula (J) can be effected via reaction of the R unsubstituted compounds with a dialkylsulfate or R' halide:

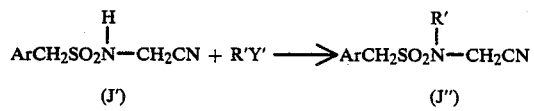

(J')    (J")

wherein Ar is as defined hereinabove and R' is as defined for R, hereinabove, but is other than hydrogen; and Y' is bromo or iodo, or R'Y' can be dialkylsulfate.

This process is especially useful to prepare the compounds of Formula (J") wherein R' is alkyl, alkenyl, alkoxyalkyl, expoxyalkylmethylene, haloalkylmethylene, or alkylthioalkyl. This process can be conducted in the same manner as described hereinabove on pages 16 to 19 with respect to the analogous acetamide process.

The compounds of Formula J" can also be prepared from the corresponding arylmethylenesulfonamide derivatives by the following schematically represented process

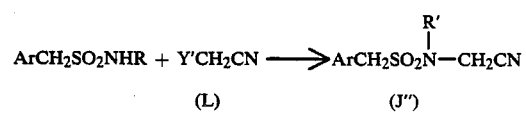

(L)    (J")

wherein Ar, R and Y' are as defined hereinabove.

This process can be conducted in the same manner as described above with respect to the analogous acetamide process but using bromo- or iodoacetonitrile (L), in place of bromo- or iodoacetamide.

The compounds of Formula I wherein $R^1$ is alkanoyl can be conveniently prepared via reaction of the corresponding $R^1$ is hydrogen compound with the appropriate anhydride under reactive conditions:

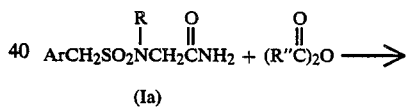

(Ia)

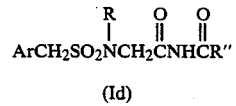

(Id)

wherein Ar and R are as defined hereinabove and R" is alkyl having 1 through 4 carbon atoms.

This process can be conducted by contacting compound (Ia) with the appropriate R"C(O) anhydride preferably in the presence of a strong acid catalyst such as, for example, sulfuric acid.

Typically, this process is conducted at temperatures in the range of about from 25° to 200° C., preferably 100° to 130° C. for about from 1 to 20 hours, preferably 2 to 4 hours using about from 1 to 10 moles of anhydride per mole of compound (Ia). Where an acid catalyst is used, about from 0.05 to 0.1 moles of catalyst is typically used per mole of compound (Ia). Suitable catalysts which can be used, include, for example, sulfuric acid, acetyl chloride, perchloric acid, and the like. Optionally, the reaction can also be conducted in a suitable organic solvent, but generally, it is preferable to simply use an excess of the anhydride as solvent.

The compounds of Formula I wherein $R^1$ is hydroxy can be conveniently prepared by treatment of the corresponding thioesters with hydroxylamine hydrochloride under reactive conditions.

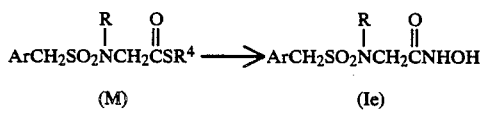

wherein Ar and R are as defined hereinabove and $R^4$ is lower alkyl.

This reaction can be conveniently effected by contacting thioester (M) with hydroxylamine hydrochloride, preferably in a suitable solvent, in the presence of a base (e.g., sodium hydroxide).

Typically, this reaction is conducted at temperatures in the range of about from 0° to 100° C., preferably 10° to 30° C., for about from 1 to 24 hours, preferably 2 to 4 hours, using about from 1 to 2, preferably 1 to 1.1 moles of hydroxylamine hydrochloride are used per mole of thioester (H). Typically about from 2 to 2.2 moles of base are used per mole of thioester (M). Suitable solvents which can be used include, for example, ethanol, methanol, glycerol, and the like. An aqueous alkanol solvent, such as aqueous ethanol has been found to function well as the solvent.

The thioesters of Formula M can be conveniently prepared from the corresponding acetyl chloride analogs:

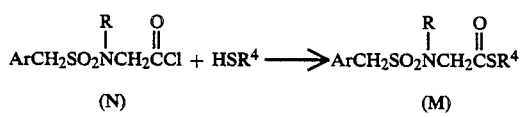

This reaction can be conducted by contacting the acetyl chloride (N) with an alkylthiol preferably in an inert organic solvent and an acid scavenger to react with HCl liberated by the reaction.

Typically, this reaction is conducted at temperatures in the range of about from 25° to 100° C., preferably 25° to 80° C. for about from 1 to 24 hours, using about from 1 to 1.5 moles of alkylthiol and about from 1 to 1.5 moles of scavenger base per mole of acetyl chloride (J). Suitable scavenger bases which can be used include, for example, triethylamine, pyridine, piperidine, and the like.

The compounds of Formula I wherein X is thioxo can be prepared via the following schematically represented process.

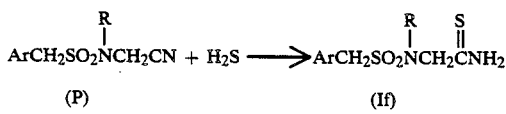

wherein Ar and R are as defined hereinabove.

The process can be effected by contacting compound (P) with hydrogen sulfide under reactive conditions, typically in the presence of a weak base and preferably in an inert organic solvent.

Typically, this process is conducted at temperatures in the range of about from 0° to 80° C., preferably about from 20° to 40° C., for about from ½ to 12 hours, preferably about from 0.5 to 3 hours, using about from 1 to 100, preferably 5 to 25, mole equivalents of sulfide per mole of compound (P) and 1 to 1.2 mole equivalents of weak base per mole of Compound (P). Suitable weak bases which can be used include, for example, triethylamine, di(isopropyl)amine, piperidine, and the like. Best results are typically obtained using triethylamine. Suitable inert organic solvents which can be used include, for example, ethanol, methanol, isopropanol, and the like, and compatible mixtures thereof.

As in the case of the "X is oxo" compounds of Formula I, it is preferable in some instances to prepare certain of the R-substituted thioamides of Formula (I) from the corresponding R-unsubstituted compound of Formula (I). This process can be schematically represented by the overall reaction equation:

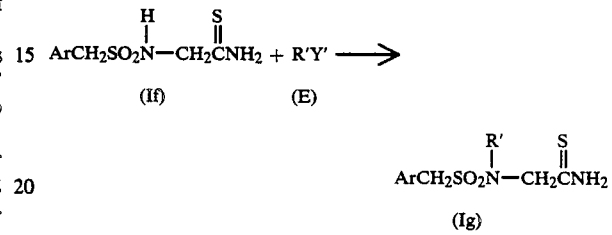

wherein Ar is as defined hereinabove and R' is as defined for R, hereinabove, but is other than hydrogen; and Y' is bromo or iodo, or R'Y' can be dialkylsulfate.

The above process is a general procedure but is especially useful to prepare the compounds of Formula (Ig) wherein R' is alkyl, alkenyl, alkoxyalkyl, hydroxyalkyl, epoxyalkylmethylene, haloalkylmethylene, cyanomethyl or alkylthioalkyl. This process can be effected as a phase transfer reaction by contacting Compound (If) with Compound (E) in water and an inert water immiscible organic solvent in the presence of base and a phase transfer agent.

This process is typically conducted at temperatures in the range of about from 0° to 80° C., preferably, 25° to 80° C., for about from 1 to 36 hours, preferably 2 to 24 hours using about from 1 to 2 moles, preferably 1 to 1.2 mole equivalents of Compound (E) and 1 to 2 mole equivalents, preferably about 1 mole equivalent of base and 0.05 to 1 mole equivalents, preferably 0.05 to 0.3 mole equivalents of phase transfer agent per mole of Compound (If).

Suitable inert water immiscible organic solvents which can be used include, for example, chloroalkanes, e.g., methylene chloride, 1,2-dichloroethane, and trichloroethane; toluene, and the like and compatible mixtures thereof. Typically, about from 1 to 8, preferably 3.5 to 5.5 liters of inert organic solvent are used per mole of Compound (If). Generally, water to immiscible solvent volume ratios of about from 1:3 to 1:20, preferably about 1:10 are used.

Suitable phase transfer agents which can be used are compounds which transfer hydrophilic ions into liquid lipophilic organic mediums and include benzyl triethylammonium chloride, methyl trioctylammonium chloride, tetrabutyl ammonium chloride, tetrabutyl ammonium bromide and the like. Very good results are typically obtained using benzyl triethylammonium chloride as the phase transfer agent.

Suitable bases which can be used include, for example, sodium hydroxide, potassium hydroxide, sodium carbonate, potassium carbonate, lithium carbonate, and the like.

The above process can also be conducted by contacting Compound (If) with Compound (E) in the presence of a strong base, such as sodium hydride, preferably in an inert organic solvent. In the case where Compound (E) is a sulfenyl halide, the reaction is preferably carried out using a weak base, such as pyridine.

This process is typically conducted at temperatures in the range of about from 0° to 100° C., preferably, 25° to 60° C., for about from 1 to 24 hours, preferably 2 to 4 hours using about from 1 to 2 moles, preferably 1 to 1.1 mole equivalents of the Compound (E) and 1 to 1.2 moles, preferably about 1 to 1.1 mole equivalents of strong base per mole of Compound (If).

Suitable strong bases which can be used include, for example, sodium hydride, lithium hydride, potassium hydride, and the like. Suitable inert organic solvents which can be used include, for example, dimethylformamide, tetrahydrofuran, dimethylsulfoxide, and the like and compatible mixtures thereof.

The salts of Formula (I) can be prepared by conventional procedures for example by treating the compound of Formula (I) with sodium hydride, or lithium diisopropylamide. Additional variation in the salt cation can also be effected by ion exchange with the appropriate ion exchange resin. Typical salt cations include for example, sodium, lithium, potassium, and the like.

General Process Conditions

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mole ratios, solvents, etc.) may vary with the particular reagents or oragnic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

Definitions

As used herein the following terms have the following meanings unless expressly stated to the contrary:

The term "lower alkyl" refers to both straight- and branched-chain alkyl groups having a total of from 1 through 6 carbon atoms, preferably 1 through 4 carbon atoms and includes primary, secondary and tertiary alkyl groups. Typical lower alkyls include, for example, methyl, ethyl, n-propyl, isopropyl, n-butyl, t-butyl.

The term "lower alkylene" refers to both straight chain and branched chain alkylene groups having 1 through 6 carbon atoms, preferably 1 through 4 carbon atoms and includes, for example,

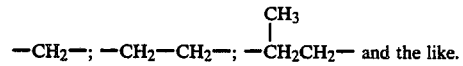

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkoxy" refers to the group —OR' wherein R' is lower alkyl.

The term "lower alkylthio" refers to the group —SR' wherein R' is lower alkyl.

The term "lower alkoxyalkyl" refers to the group R'OR"— wherein R' and R" are independently straight chain or branched chain alkyl groups having 1 through 3 carbon atoms.

The term "alkanoyl" refers to the group

wherein R' is alkyl.

The term "lower alkylthioalkyl" refers to the group R'SR"— wherein R' and R" are independently straight chain or branched chain alkyl groups having 1 through 3 carbon atoms.

The term "haloalkylmethyl" or (haloalkyl)methyl refers to the group having the formula R'''CH$_2$— wherein R''' is a branched or straight chain haloalkyl. The term haloalkylmethyl includes, for example, 2,2-dichloroethyl; 2-chloropropyl; and the like.

The term "halo" refers to the group of fluoro, chloro, bromo and iodo.

The term (N-methyl-3-trifluoromethylbenzylsulfonamido)acetonitrile refers to the compound having the structural formula

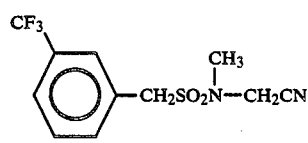

The term "room temperature" or "ambient temperature" refers to about 20°–25° C.

The term (N-methyl-3-trifluoromethyl-benzylsulfonamido)acetamide refers to the compound having the structural formula:

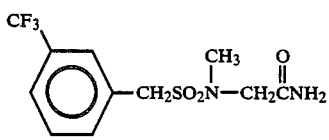

The term "2-propynyl" or "propargyl" refers to HC≡CCH$_2$—. The term "(cycloalkyl)alkyl" or "cycloalkylalkyl" refers to the group R'''R'— wherein R''' is cycloalkyl and R' is alkyl.

The term "compatible salts" refers to salts which do not significantly alter the herbicidal properties of the parent compound. Suitable salts include cation salts such as, for example, the cation salts of lithium, sodium, potassium, alkali earth metals, ammonia, isopropylammonium, quaternary ammonium salts, and the like.

Utility

The herbicidal compounds of the invention exhibit excellent selective pre- and post-emergence phytoxicity against barnyardgrass (*Echinochloa crusgalli*) also known as watergrass, and have excellent crop safety. The compounds are especially useful for the elimination and prevention of barnyardgrass in rice crops.

Generally, for post-emergent applications, the herbicidal compounds are applied directly to the foliage or other plant parts. For pre-emergence applications, the herbicidal compounds are applied prospectively to the growth medium (habitat) for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for preemergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages the compounds of the present invention can be expected to exhibit plant growth regulating activity and can be used to alter the normal growth pattern of plants. For example, a number of the compounds show significant capacity to retard root growth.

As in the case of herbicides plant growth regulators can be applied in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Preparation(s) and Example(s). Wherein, unless expressly stated to the contrary, all temperatures and temperature ranges refer to the Centigrade system and the term "ambient" or "room temperature" refers to about 20° to 25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLES AND PREPARATIONS

Preparation 1

3-Trifluoromethylbenzylsulfonyl Chloride (a) A mixture containing 50 g of 3-trifluoromethylbenzyl chloride and 32.4 g of sodium sulfite in 200 ml of water was refluxed for five hours and then concentrated by evaporation. The concentrate was then filtered to collect the precipitate (product). The precipitate was then washed with ethyl ether and then dried in a vacuum oven affording 61 g of sodium 3-trifluoromethylbenzylsulfonate.

(b) 10 g of sodium 3-trifluoromethylbenzylsulfonate was slowly added to 17.7 ml (29.1 g) of phosphorous oxychloride. The resulting slurry was stirred at 100° to 105° C. for five hours. The reaction mixture was then cooled and filtered. The filter cake was washed with methylene chloride, the washings were combined with the filtrate and then evaporated to dryness affording 8.9 g of 3-trifluoromethylbenzylsulfonyl chloride.

EXAMPLE 1

Ethyl (N-methyl-3-trifluoromethylbenzylsulfonamido)acetate

In this example, 22 g of 3-trifluoromethylbenzylsulfonyl chloride was added cautiously to a solution containing 27 g of the hydrochloride salt of sarcosine ethyl ester and 12 g of potassium carbonate in 90 ml of water at room temperature. The reaction mixture was heated to about 70° C. and maintained at this temperature for about four hours. The mixture was allowed to cool and then extracted with ethyl ether. The ethyl ether extract was dried over magnesium sulfate, filtered, and evaporated to dryness yielding 9.5 g of the title compound as an off-white solid.

Similarly, by generally applying the above procedure using the appropriate substituted benzylsulfonyl chloride starting material, the following compounds can be prepared:
ethyl (N-methyl-3-fluorobenzylsulfonamido)acetate;
ethyl (N-methyl-3-iodobenzylsulfonamido)acetate;
ethyl (N-methyl-3-ethylbenzylsulfonamido)acetate;
ethyl (N-methyl-3-t-butylbenzylsulfonamido)acetate;
ethyl (N-methyl-3-butylbenzylsulfonamido)acetate;
ethyl (N-methyl-3-ethoxybenzylsulfonamido)acetate;
ethyl (N-methyl-3,4,5-trifluorobenzylsulfonamido)acetate;
ethyl (N-methyl-2-trifluoromethylbenzylsulfonamido)acetate;
ethyl (N-methyl-2-chlorobenzylsulfonamido)acetate;
ethyl (N-methyl-pentafluorobenzylsulfonamido)acetate;
ethyl (N-methyl-3-nitrobenzylsulfonamido)acetate;
ethyl (N-methyl-3-bromobenzylsulfonamido)acetate;
ethyl (N-methyl-3-fluorobenzylsulfonamido)acetate;
ethyl (N-methyl-3-methoxybenzylsulfonamido)acetate;
ethyl (N-methyl-2,5-di-trifluoromethylbenzylsulfonamido)acetate;
ethyl (N-methyl-3,5-di-trifluoromethylbenzylsulfonamido)acetate;
ethyl (N-methyl-3-trifluoromethyl-5-bromobenzylsulfonamido)acetate;
ethyl (N-methyl-3,4-ditrifluoromethylbenzylsulfonamido)acetate;
ethyl (N-methyl-2,6-dichlorobenzylsulfonamido)acetate;
ethyl (N-methyl-2-chloro-3-methylbenzylsulfonamido)acetate;
ethyl (N-methyl-2-chloro-4-trifluoromethylbenzylsulfonamido)acetate;
ethyl (N-methyl-2-chloro-3-bromobenzylsulfonamido)acetate;
ethyl (N-methyl-3-chloro-5-methoxy-benzylsulfonamido)acetate;
ethyl (N-methyl-2-chloro-4-1′,2′,2′-trifluoroethylbenzylsulfonamido)acetate;
ethyl (N-methyl-2,4,5-trifluorobenzylsulfonamido)acetate.

EXAMPLE 2

(N-methyl-3-trifluoromethylbenzylsulfonamido)acetamide. Hydrate

In this example, 3.39 g of ethyl (N-methyl-3-trifluoromethylbenzylsulfonamido)acetate was ground to a powder and combined with about 50 ml of ammonium hydroxide at room temperature. The reaction mixture was heated to about 40° C. and maintained at this temperature for about three hours. The precipitate was collected, washed with water and triturated with ethyl ether to afford 1.4 g of white solid; m.p. 156° to 159° C.

Similarly, by applying the general procedure of this example using the corresponding substituted ester starting materials the following compounds can be prepared:
(N-methyl-3-fluorobenzylsulfonamido)acetamide;
(N-methyl-3-iodobenzylsulfonamido)acetamide;
(N-methyl-3-ethylbenzylsulfonamido)acetamide;
(N-methyl-3-t-butylbenzylsulfonamido)acetamide;
(N-methyl-3-n-butylbenzylsulfonamido)acetamide;
(N-methyl-3-ethoxybenzylsulfonamido)acetamide;
(N-methyl-3,4,5-trifluorobenzylsulfonamido)acetamide;
(N-methyl-2-trifluoromethylbenzylsulfonamido)acetamide;
(N-methyl-2-chlorobenzylsulfonamido)acetamide;
(N-methyl-pentafluorobenzylsulfonamido)acetamide;
(N-methyl-3-nitrobenzylsulfonamido)acetamide;
(N-methyl-3-bromobenzylsulfonamido)acetamide;
(N-methyl-3-fluorobenzylsulfonamido)acetamide;
(N-methyl-3-methoxybenzylsulfonamido)acetamide;
(N-methyl-2,5-di-trifluoromethylbenzylsulfonamido)acetamide;
(N-methyl-3,5-di-trifluoromethylbenzylsulfonamido)acetamide;
(N-methyl-3-trifluoromethyl-5-bromobenzylsulfonamido)acetamide;
(N-methyl-3,4-di-trifluoromethylbenzylsulfonamido)acetamide;
(N-methyl-2,6-dichlorobenzylsulfonamido)acetamide;
(N-methyl-2-chloro-3-methylbenzylsulfonamido)acetamide;
(N-methyl-2-chloro-4-trifluoromethylbenzylsulfonamido)acetamide;
(N-methyl-2-chloro-3-bromobenzylsulfonamido)acetamide;
(N-methyl-2-chloro-4-1′,2′,2′-trifluoroethylbenzylsulfonamido)acetamide;
(N-methyl-2,4,5-trifluorobenzylsulfonamido)acetamide; and
(N-methyl-2,3,5,6-tetrafluorobenzylsulfonamido)acetamide.

EXAMPLE 3

(N-Allyl-3-Trifluoromethylbenzylsulfonamido)acetamide 2.96 g of 3-trifluoromethylbenzylsulfonamidoacetamide was dissolved in 10 ml of dry dimethylformamide. To this ice-cooled solution was added 0.24 g of sodium hydride. The reaction mixture was stirred for 15 minutes at room temperature and then 0.95 ml of allyl bromide dissolved in 5 ml of dimethylformamide was added dropwise. Reaction was essentially instantaneous. After about 30 minutes, the reaction mixture was diluted with 150 ml of water and extracted twice with 75 ml portions of diethyl ether. Petroleum ether was added to the combined ether phases until cloudiness occurred, and this solution was washed with 100 ml of water. The organic phase was dried over magnesium sulfate and stripped to a white solid. Trituration with carbon tetrachloride afforded 2.8 g of the title compound, m.p. 91° to 92° C.

Similarly by adapting the general procedure used above using the appropriate starting materials (diethyl sulfate can also be used to prepare the N-ethyl derivatives as well as ethyl iodide or bromide) the following compounds can be prepared:

(N-allyl-3-difluoromethylbenzylsulfonamido)acetamide;
(N-allyl-3-ethylbenzylsulfonamido)acetamide;
(N-allyl-3-t-butylbenzylsulfonamido)acetamide;
(N-allyl-3-methylbenzylsulfonamido)acetamide;
(N-allyl-3-ethoxybenzylsulfonamido)acetamide;
(N-allyl-2-trifluoromethylbenzylsulfonamido)acetamide;
(N-allyl-3-2',2'-difluoroethylbenzylsulfonamido)acetamide;
(N-allyl-2,3,6-trichlorobenzylsulfonamido)acetamide;
(N-allyl-3-methoxybenzylsulfonamido)acetamide;
(N-allyl-3-fluorobenzylsulfonamido)acetamide;
(N-allyl-3-bromobenzylsulfonamido)acetamide;
(N-allyl-3-nitrobenzylsulfonamido)acetamide;
(N-allyl-3-ethoxybenzylsulfonamido)acetamide;
(N-allyl-2,5-di-trifluoromethylbenzylsulfonamido)acetamide;
(N-allyl-3-trifluoromethyl-5-bromobenzylsulfonamido)acetamide;
(N-allyl-3,4-ditrifluoromethylbenzylsulfonamido)acetamide;
(N-allyl-2,6-dichlorobenzylsulfonamido)acetamide;
(N-allyl-2-chloro-3-methylbenzylsulfonamido)acetamide;
(N-allyl-2-chloro-4-trifluoromethylbenzylsulfonamido)acetamide;
(N-allyl-2-chloro-3-bromobenzylsulfonamido)acetamide;
(N-allyl-2-chloro-4-1',2',2'trifluoroethylbenzylsulfonamido)acetamide;
(N-allyl-2-trifluoromethylbenzylsulfonamido)acetamide;
(N-allyl-3-methylbenzylsulfonamido)acetamide;
(N-allyl-3-trifluoromethyl-5-methoxybenzylsulfonamido)acetamide;
(N-allyl-3-trifluoromethyl-4-chlorobenzylsulfonamido)acetamide;
(N-ethyl-3-fluorobenzylsulfonamido)acetamide;
(N-ethyl-3-iodobenzylsulfonamido)acetamide;
(N-ethyl-3-ethylbenzylsulfonamido)acetamide;
(N-ethyl-3-t-butylbenzylsulfonamido)acetamide;
(N-ethyl-3-butylbenzylsulfonamido)acetamide;
(N-ethyl-3-ethoxybenzylsulfonamido)acetamide;
(N-ethyl-3-propoxybenzylsulfonamido)acetamide;
(N-ethyl-2-trifluoromethylbenzylsulfonamido)acetamide;
(N-ethyl-2-chlorobenzylsulfonamido)acetamide;
(N-ethyl-pentafluorobenzylsulfonamido)acetamide;
(N-ethyl-3-nitrobenzylsulfonamido)acetamide;
(N-ethyl-3-fluoromethylbenzylsulfonamido)acetamide;
(N-ethyl-3-methoxybenzylsulfonamido)acetamide;
(N-ethyl-2-methylbenzylsulfonamido)acetamide;
(N-ethyl-3-chlorobenzylsulfonamido)acetamide;
(N-ethyl-3-bromobenzylsulfonamido)acetamide;
(N-ethyl-2-trifluoromethyl-4-butoxybenzylsulfonamido)acetamide;
(N-ethyl-2-chloro-3-methoxybenzylsulfonamido)acetamide;
(N-ethyl-2,3-di-trifluoromethylbenzylsulfonamido)acetamide;
(N-ethyl-2,4-di-trifluoromethylbenzylsulfonamido)acetamide;
(N-ethyl-2,5-di-trifluoromethylbenzylsulfonamido)acetamide;
(N-ethyl-3,4-dichlorobenzylsulfonamido)acetamide;
(N-ethyl-2-chloro-6-trifluoromethyl-benzylsulfonamido)acetamide;
(N-ethyl-2-butyl-3-chlorobenzylsulfonamido)acetamide;
(N-ethyl-2-chloro-4-trifluoromethylbenzylsulfonamido)acetamide;
(N-ethyl-2-chloro-3-bromobenzylsulfonamido)acetamide;
(N-ethyl-3-chloro-5-butylbenzylsulfonamido)acetamide;
(N-ethyl-2,4,5-trifluorobenzylsulfonamido)acetamide;
(N-ethyl-pentafluorophenylmethylsulfonamido)acetamide;
(N-propyl-3-trifluoromethylbenzylsulfonamido)acetamide;
(N-butyl-3-difluoromethylbenzylsulfonamido)acetamide;
(N-pentyl-3-ethylbenzylsulfonamido)acetamide;
(N-propargyl-3-ethylbenzylsulfonamido)acetamide;
(N-pentyl-2-chlorobenzylsulfonamido)acetamide;
(N-hexyl-3-bromobenzylsulfonamido)acetamide;
(N-propyl-3,4-di-trifluoromethylbenzylsulfonamido)acetamide;
(N-isopropyl-2,6-dichlorobenzylsulfonamido)acetamide;
(N-butyl-2-chloro-3-methylbenzylsulfonamido)acetamide;
(N-4-iodopropargyl-2-chloro-4-trifluoromethylbenzylsulfonamido)acetamide;
(N-pentyl-2-chloro-3-bromobenzylsulfonamido)acetamide;
(N-but-3-enyl-2-bromo-3-trifluoromethylbenzylsulfonamido)acetamide;
(N-propyl-3-trifluoromethylbenzylsulfonamido)acetamide;
(N-isopropyl-3-difluoromethylbenzylsulfonamido)acetamide;
(N-pentyl-3-ethylbenzylsulfonamido)acetamide;
(N-cyclopropylmethyl-3-t-butylbenzylsulfonamido)acetamide;
(N-hexyl-3-ethoxybenzylsulfonamido)acetamide;
(N-propyl-2-chlorobenzylsulfonamido)acetamide;
(N-butyl-3-methoxybenzylsulfonamido)acetamide;
(N-pentyl-3-fluorobenzylsulfonamido)acetamide;
(N-hexyl-3-bromobenzylsulfonamido)acetamide;
(N-cyclohexyl-3-nitrobenzylsulfonamido)acetamide;
(N-cyclopropylmethyl-2,5-di-trifluoromethylbenzylsulfonamido)acetamide;
(N-propyl-3-chloro-4-methoxybenzylsulfonamido)acetamide;
(N-isopropyl-2-chloro-6-methoxybenzylsulfonamido)acetamide;
(N-butyl-2-chloro-3-methylbenzylsulfonamido)acetamide;
(N-isopropyl-2-chloro-4-trifluoromethylbenzylsulfonamido)acetamide;
(N-pentyl-2-fluoro-3-chlorobenzylsulfonamido)acetamide;
(N-hexyl-2-fluoro,3,4-dibromobenzylsulfonamido)acetamide;
(N-cyanomethyl-3-trifluoromethylbenzylsulfonamido)acetamide;
(N-cyanomethyl-3-difluoromethylbenzylsulfonamido)acetamide;
(N-cyanomethyl)-3-ethylbenzylsulfonamido)acetamide;
(N-cyanomethyl-3-t-butylbenzylsulfonamido)acetamide;
(N-cyanomethyl-3-butylbenzylsulfonamido)acetamide;
(N-cyanomethyl-3-ethoxybenzylsulfonamido)acetamide;

(N-cyanomethyl-2-trifluoromethylbenzylsulfonamido)acetamide;
(N-cyanomethyl-3-1',2'-difluoroethylbenzylsulfonamido)acetamide;
(N-cyanomethyl-3-methoxybenzylsulfonamido)acetamide;
(N-cyanomethyl-3-fluorobenzylsulfonamido)acetamide;
(N-cyanomethyl-3-bromobenzylsulfonamido)acetamide;
(N-cyanomethyl-3-nitrobenzylsulfonamido)acetamide;
(N-cyanomethyl-3-propoxybenzylsulfonamido)acetamide;
(N-cyanomethyl-2,5-di-trifluoromethylbenzylsulfonamido)acetamide;
(N-cyanomethyl-2,4-di-trifluoromethylbenzylsulfonamido)acetamide;
(N-cyanomethyl-3,5-di-difluoromethylbenzylsulfonamido)acetamide;
(N-cyanomethyl-3-chloro-4-methoxybenzylsulfonamido)acetamide;
(N-cyanomethyl-2,6-dichlorobenzylsulfonamido)acetamide;
(N-cyanomethyl-2-iodo-3-chlorobenzylsulfonamido)acetamide;
(N-cyanomethyl-2-chloro-4-trifluoromethylbenzylsulfonamido)acetamide;
(N-cyanomethyl-2-fluoro-3-chlorobenzylsulfonamido)acetamide;
(N-cyanomethyl-3-trifluoromethyl-5-iodobenzylsulfonamido)acetamide;
(N-cyanomethyl-4-chloro-3-trifluoromethylbenzylsulfonamido)acetamide;
(N-cyanomethyl-2,4,5-trifluorobenzylsulfonamido)acetamide;
(N-methoxymethyl-3-trifluoromethylbenzylsulfonamido)acetamide;
(N-1'-methoxyethyl-3-trifluoromethylbenzylsulfonamido)acetamide;
(N-3'-propoxypropyl-3-trifluoromethylbenzylsulfonamido)acetamide;
(N-2',3'-epoxypropyl-3-trifluoromethylbenzylsulfonamido)acetamide;
(N-3',4'-epoxypentyl-3-trifluoromethylbenzylsulfonamido)acetamide;
(N-methylthiomethyl-3-trifluoromethylbenzylsulfonamido)acetamide;
(N-2'-ethylthiopropyl-3-trifluoromethylbenzylsulfonamido)acetamide;
(N-allyl-3-trifluoromethylbenzylsulfonamido)acetamido;
(N-hex-4-enyl-3-trifluoromthylbenzylsulfonamido)acetamide;
(N-2'-hydroxyethyl-3-trifluoromethylbenzylsulfonamido)acetamide;
(N-2',2'-dichloroethyl-3-trifluoromethylbenzylsulfonamido)acetamide;
(N-2',3'-epoxypropyl-3-ethylbenzylsulfonamido)acetamide;
(N-5α,6'-epoxyhexyl-3-t-butylbenzylsulfonamido)acetamide;
(N-2',2'-dichloroethyl-3-ethoxybenzylsulfonamido)acetamide;
(N-hexylthiomethyl-2-trifluoromethylbenzylsulfonamido)acetamide;
(N-isopropylthiomethyl-2-trifluoromethylbenzylsulfonamido)acetamide;
(N-6'-methylthiohexyl-2-chlorobenzylsulfonamido)acetamide;
(N-methoxymethyl-2-2',3'-difluoropropylbenzylsulfonamido)acetamide;
(N-2'-methoxyethyl-3-fluorobenzylsulfonamido)acetamide;
(N-2'-propoxypropyl-3-methoxybenzylsulfonamido)acetamide;
(N-2',3'-epoxypropyl-3-fluorobenzylsulfonamido)acetamide;
(N-3',4'-epoxybutyl-3-bromobenzylsulfonamido)acetamide;
(N-3'-hydroxypropyl-3-nitrobenzylsulfonamido)acetamide;
(N-pentylthiomethyl-3,5-di-trifluoromethylbenzylsulfonamido)acetamide;
(N-2'-propylthiobutyl-2,5-di-trifluoromethylbenzylsulfonamido)acetamide;
(N-pent-2-enyl-3,5-di-difluoromethylbenzylsulfonamido)acetamide;
(N-4'-hydroxybutyl-3-chloro-4-methoxybenzylsulfonamido)acetamide;
(N-cyclopentyl-3-chlorobenzylsulfonamido)acetamide;
(N-2'-hydroxyethyl-3-chlorobenzylsulfonamido)acetamide;
(N-isopropylthiomethyl-2-chloro-4-trifluoromethylbenzylsulfonamido)acetamide;
(N-2'-methylthiopropyl-2-chloro-3-bromobenzylsulfonamido)acetamide;
(N-pentoxymethyl-3-nitrobenzylsulfonamido)acetamide;
(N-3'-butoxypropyl-3-trifluoromethylbenzylsulfonamido)acetamide; and
(N-isopropoxymethyl-3-difluoromethylbenzylsulfonamido)acetamide.

EXAMPLE 4

(N-Cyclopropyl-3-Trifluoromethylbenzylsulfonamido)-Acetamide

This example illustrates a procedure which can be used to prepare the title compound.

(a) In this example, 5.3 g of cyclopropylamine is mixed with 9.4 g of triethylamine and then added dropwise to a solution containing 20 g of 3-trifluoromethylbenzylsulfonyl chloride in methylene chloride at 0° C. The resulting reaction mixture is stirred at room temperature (i.e., about 20°-25° C.) for 3 hours. The reaction mixture is washed with saturated aqueous ammonium chloride and then with aqueous 1 wt.% hydrochloric acid until it was neutral. The organic layer is separated, washed twice with 50 ml of aqueous saturated sodium chloride solution, dried over magnesium sulfate and then evaporated to dryness affording 20 g of N-cyclopropyl-3-trifluoromethylbenzylsulfonamide.

(b) 0.26 Gram of sodium hydride is added portionwise to a solution containing 2.77 g of N-cyclopropyl-3-trifluoromethylbenzylsulfonamide in 50 ml of dimethylformamide over an ice bath. The mixture is stirred 15 minutes at 0° C. and then 0.0105 moles of bromoacetamide is added dropwise with cooling. The mixture is stirred overnight at room temperature. Water is then added. This will result in the formation of a precipitate and oil. Water is continued to be added until no further precipitate or oil is formed. The mixture is cooled over an ice bath and then filtered. The filter cake is dissolved in hot cyclohexane and then recrystallized affording the title compound.

Similarly, by following the same procedure using the corresponding substituted benzylsulfonyl chlorides as starting material, the following compounds can be prepared:

(N-cyclopropyl-3-chlorobenzylsulfonamido)acetamide;
(N-cyclopropyl-2-trifluoromethylbenzylsulfonamido)acetamide;
(N-cyclopropyl-2-chloro-5-trifluoromethylbenzylsulfonamido)acetamide;
(N-cyclopropyl-2,3-dichloro-5-trifluoromethylbenzylsulfonamido)acetamide;
(N-cyclopropyl-pentafluorophenylmethylsulfonamido)acetamide;

EXAMPLE 5

(N-Ethyl-3-Trifluoromethylbenzylsulfonamido)Acetonitrile

In this example 2 g of 3-trifluoromethylbenzylsulfonamidoacetamide was dissolved in 30 ml of dichloromethane. To this was added 0.32 g of sodium hydroxide dissolved in a minimum amount of water and 0.46 of benzyltriethylammonium chloride. A solution of 1.1 ml of diethylsulfate in 5 ml of dichloromethane was added dropwise. The reaction mixture was stirred overnight at room temperature. Water was added to the reaction mixture, and the dichloromethane layer was separated. The water phase is extracted with dichloromethane. The organic phases are combined, dried over magnesium sulfate, filtered and stripped. Trituration of the resulting solid residue yielded 1.4 g of title compound as a white solid; m.p. 67° to 68.5° C.

EXAMPLE 6

(N-Methyl-3-trifluoromethylbenzylsulfonamido)acetonitrile

In this example 21 ml (0.15 mole) of triethylamine was added over a 5 minute period to a cooled solution containing 16 g (0.15 mole) of the hydrochloride salt of methylaminoacetonitrile in 150 ml of methylene chloride. The mixture was stirred at 20° C. for 15 minutes and then 7.9 g (0.1 mole) of pyridine was added. Then 25.9 g (0.1 mole) of 3-trifluoromethylbenzylsulfonyl-chloride dissolved in about 50 ml methylene chloride was added to the reaction mixture. The reaction mixture was maintained at 20° C. during the addition and then refluxed for three hours. The mixture was cooled to room temperature and washed once with 200 ml of water and then washed twice with 100 ml of aqueous 5 wt. % hydrochloric acid. The washed mixture was dried over magnesium sulfate and evaporated under vacuum affording 28.2 g of the title compound as a solid residue.

EXAMPLE 7

(N-Methyl-3-trifluoromethylbenzylsulfonamido)acetamide

In this example 11.68 g of (N-methyl-3-trifluoromethylenzylsulfonamido)acetonitrile was added to a mixture of 24 g of concentrated sulfuric acid and 0.04 g of sulfur. The resulting slurry was stirred and warmed with a heat gun until solution occurred. The reaction mixture then began foaming. After the foaming subsided, the reaction mixture was diluted with 200 ml of water. The off-white precipitate which formed was vacuum filtered and triturated with diethyl ether to yield 10.5 g of the title compound as a white powder; m.p. 146° to 148° C.

(N-ethyl-3-trifluoromethylbenzylsulfonamido)acetamide, m.p. 122° to 123° C.; (N-methyl-2-chloro-5-trifluoromethylbenzylsulfonamido)acetamide, m.p. 171° to 177° C. and (N-methyl-3,5-dichlorobenzylsulfonamido)acetamide, m.p. 155° to 162° C. were also prepared by this general procedure using the corresponding acetonitrile analog.

Example 8

(N-Methyl-3-trifluoromethylbenzylsulfonamido)-N-hydroxy-acetamide (a) In this example 3.2 ml of ethylthiol (0.06 mole) was added to a stirred solution containing 14.1 g of (N-methyl-3-trifluoromethylbenzylsulfonamido)acetyl chloride in 200 ml of methylene chloride at room temperature (about 20°-25° C.). Then 4.8 g of triethylamine was slowly added dropwise. The mixture was stirred overnight (about 18 hours) at room temperature and then evaporated to remove solvent. The concentrate was mixed with ethyl ether, washed twice with 20 ml aqueous 5 wt.% hydrochloric acid, twice with 20 ml of water and then dried over magnesium sulfate and filtered. The filtrate was evaporated to dryness affording 7 grams of an oil which was determined to contain more than 50% S-ethyl (N-methyl-3-trifluoromethylbenzylsulfonamido)-thioacetate.

(b) The oil residue, containing about 4.5 g of the thioacetate, was used as starting material for this step. 0.88 Gram of $NH_2OH \cdot HCl$ was slowly added to aqueous ethanol, obtained by mixing 2 ml of water with 1.5 ml of absolute ethanol, while cooling over an ice and water bath. A sodium hydroxide solution containing 1.1 g of sodium hydroxide in 2.5 ml of water was slowly added dropwise. After addition of the sodium hydroxide was completed, the cooling bath was removed and a solution of the oil residue of step (a), dissolved in 3 ml of absolute ethanol, was slowly added dropwise. The mixture was stirred two hours at room temperature and then filtered. The recovered solids were washed with water and dried under vacuum at 48° C. overnight (about 18 hours). The dried solids were recrystallized from an ethanol and water solution and again dried overnight at 48° C. under vacuum affording 0.88 g of the title compound as a white solid m.p. 128°-129° C.

Similarly, by applying the same procedure using the corresponding thioester or acetyl chloride analogs, the corresponding N-hydroxyamide analogs of the compounds described hereinabove in Examples 2, 3, 4, and 7 can be prepared, for example:

(N-methyl-3-fluorobenzylsulfonamido)-N-hydroxy-acetamide;
(N-methyl-3-iodobenzylsulfonamido)-N-hydroxy-acetamide;
(N-methyl-3-ethylbenzylsulfonamido)-N-hydroxy-acetamide;
(N-methyl-3-t-butylbenzylsulfonamido)-N-hydroxy-acetamide;
(N-methyl-3-butylbenzylsulfonamido)-N-hydroxy-acetamide;
(N-methyl-3-ethoxybenzylsulfonamido)-N-hydroxy-acetamide;
(N-methyl-3,4,5-trifluorobenzylsulfonamido)-N-hydroxy-acetamide;
(N-methyl-2-trifluoromethylbenzylsulfonamido)-N-hydroxy-acetamide;

(N-methyl-2-chlorobenzylsulfonamido)-N-hydroxyacetamide;
(N-methyl-pentafluorobenzylsulfonamido)-N-hydroxyacetamide.

Example 9

N-Acetyl-(N-methyl-3-trifluoromethylbenzylsulfonamido)-acetamide

In this example, a catalytic amount (about 4 drops) of concentrated sulfuric acid was added to a suspension of 3.5 g of (N-methyl-3-trifluoromethylbenzylsulfonamido)-acetamide in 7 mls (7.6 g) of acetic anhydride at room temperature. The mixture was heated for 2 hours at about 138° C. and then poured into ice water and extracted into methylene chloride. The methylene chloride extract was washed with aqueous 5 wt.% sodium bicarbonate solution, dried over magnesium sulfate and evaporated to dryness affording 3.4 g of a white solid. The solid was triturated with ethyl ether affording 2.17 g of the title compound.

Similarly, by applying the same procedure, using the corresponding amide analog and the appropriate anhydride as starting materials, the corresponding N-acetyl, N-propionyl, and N-valeryl analogs of products, described hereinabove in Examples 2, 3, 4 and 7, can be prepared, for example:

N-acetyl-(N-allyl-3-difluoromethylbenzylsulfonamido)acetamide;
N-acetyl-(N-ethyl-3-ethylbenzylsulfonamido)acetamide;
N-acetyl-(N-propargyl-3-t-butylbenzylsulfonamido)acetamide;
N-acetyl-(N-3'-iodopropargyl-3-butylbenzylsulfonamido)acetamide;
N-acetyl-(N-but-3-enyl-3-ethoxybenzylsulfonamido)acetamide;
N-acetyl-(N-cyclopropyl-2-trifluoromethylbenzylsulfonamido)acetamide;
N-acetyl-(N-allyl-3-2',2'-difluoroethylbenzylsulfonamido)acetamide;
N-acetyl-(N-methyl-2,3,6-trichlorobenzylsulfonamido)acetamide;
N-acetyl-(N-isopropyl-3-methoxybenzylsulfonamido)acetamide;
N-propionyl-(N-methyl-3-trifluoromethylbenzylsulfonamido)acetamide;
N-propionyl-(N-allyl-3-difluoromethylbenzylsulfonamido)acetamide;
N-propionyl-(N-ethyl-3-ethylbenzylsulfonamido)acetamide;
N-propionyl-(N-propargyl-3-t-butylbenzylsulfonamido)acetamide;
N-propionyl-(N-3'-iodopropargyl-3-butylbenzylsulfonamido)acetamide;
N-propionyl-(N-propyl-3-ethoxybenzylsulfonamido)acetamide;
N-propionyl-(N-butyl-2-trifluoromethylbenzylsulfonamido)acetamide;
N-propionyl-(N-methyl-3-2',2'-difluoroethylbenzylsulfonamido)acetamide;
N-propionyl-(N-cyclopropyl-2,3,6-trichlorobenzylsulfonamido)acetamide;
N-propionyl-(N-isopropyl-3-methoxybenzylsulfonamido)acetamide;
N-valeryl-(N-isopropyl-3-trifluoromethylbenzylsulfonamido)acetamide;
N-valeryl-(N-allyl-3-difluoromethylbenzylsulfonamido)acetamide;
N-valeryl-(N-ethyl-3-ethylbenzylsulfonamido)acetamide;
N-valeryl-(N-propargyl-3-t-butylbenzylsulfonamido)acetamide;
N-valeryl-(N-3'-iodopropargyl-3-butylbenzylsulfonamido)acetamide;
N-valeryl-(N-propyl-3-ethoxybenzylsulfonamido)acetamide;
N-valeryl-(N-methyl-2-trifluoromethylbenzylsulfonamido)acetamide;
N-valeryl-(N-butyl-3-2',2'-difluoroethylbenzylsulfonamido)acetamide;
N-valeryl-(N-cyclopropyl-2,3,6-trichlorobenzylsulfonamido)acetamide; and
N-valeryl-(N-isopropyl-3-methoxybenzylsulfonamido)acetamide.

Example 10

(N-Methyl-3-trifluoromethylbenzylsulfonamido)thioacetamide

In this example, 2.1 ml of triethylamine was added to a solution of 4.5 g of (N-methyl-3-trifluoromethylbenzylsulfonamido)acetonitrile in 80 ml of absolute ethanol. Gaseous hydrogen sulfide was then bubbled into the stirred reaction mixture until no further precipitation occurred; about forty five minutes. The precipitate was vacuum filtered, washed with ethyl ether and dried to afford 3.8 g of the title compound as a white solid.

Similarly, the following compounds can be prepared by adapting the above procedure using the corresponding acetonitrile derivatives as starting materials;

(N-methyl-3-fluorobenzylsulfonamido)thioacetamide;
(N-methyl-3-iodobenzylsulfonamido)thioacetamide;
(N-methyl-3-ethylbenzylsulfonamido)thioacetamide;
(N-methyl-3-t-butylbenzylsulfonamido)thioacetamide;
(N-methyl-3-butylbenzylsulfonamido)thioacetamide;
(N-methyl-3-ethoxybenzylsulfonamido)thioacetamido;
(N-methyl-3,4,5-trifluorobenzylsulfonamido)thioacetamide;
(N-methyl-2-trifluoromethylbenzylsulfonamido)thioacetamide;
(N-methyl-2-chlorobenzylsulfonamido)thioacetamide;
(N-methyl-pentafluorobenzylsulfonamido)thioacetamide;
(N-methyl-3-nitrobenzylsulfonamido)thioacetamide;
(N-methyl-3-bromobenzylsulfonamido)thioacetamide;
(N-methyl-2-methylbenzylsulfonamido)thioacetamide;
(N-methyl-3-methoxybenzylsulfonamido)thioacetamide;
(N-methyl-2,5-di-trifluoromethylbenzylsulfonamido)thioacetamide;
(N-methyl-3,5-di-trifluoromethylbenzylsulfonamido)thioacetamide;
(N-methyl-3-trifluoromethyl-5-bromobenzylsulfonamido)thioacetamide;
(N-methyl-3,4-di-trifluoromethylbenzylsulfonamido)thioacetamide;
(N-methyl-2,6-dichlorobenzylsulfonamido)thioacetamide;
(N-methyl-2-chloro-3-methylbenzylsulfonamido)thioacetamide;
(N-methyl-2-chloro-4-trifluoromethylbenzylsulfonamido)thioacetamide;
(N-methyl-2-chloro-3-bromobenzylsulfonamido)thioacetamide;

(N-methyl-2-chloro-4-1,2',2'trifluoroethylbenzylsulfonamido)thioacetamide;
(N-methyl-2,4,5-trifluorobenzylsulfonamido)thioacetamide;
(N-ethyl-3-trifluoromethylbenzylsulfonamido)thioacetamide;
(N-ethyl-3-fluorobenzylsulfonamido)thioacetamide;
(N-ethyl-3-iodobenzylsulfonamido)thioacetamide;
(N-ethyl-3-ethylbenzylsulfonamido)thioacetamide;
(N-ethyl-3-t-butylbenzylsulfonamido)thioacetamide;
(N-ethyl-3-butylbenzylsulfonamido)thioacetamide;
(N-ethyl-3-ethoxybenzylsulfonamido)thioacetamide;
(N-ethyl-3-propoxybenzylsulfonamido)thioacetamide;
(N-ethyl-2-trifluoromethylbenzylsulfonamido)thioacetamide;
(N-ethyl-2-chlorobenzylsulfonamido)thioacetamide;
(N-ethyl-pentafluorobenzylsulfonamido)thioacetamide;
(N-ethyl-3-nitrobenzylsulfonamido)thioacetamide;
(N-ethyl-3-fluoromethylbenzylsulfonamido)thioacetamide;
(N-ethyl-2-methoxybenzylsulfonamido)thioacetamide;
(N-ethyl-2-methylbenzylsulfonamido)thioacetamide;
(N-ethyl-3-chlorobenzylsulfonamido)thioacetamide;
(N-ethyl-3-bromobenzylsulfonamido)thioacetamide;
(N-ethyl-3-trifluoromethyl-4-butoxybenzylsulfonamido)thioacetamide;
(N-ethyl-2-chloro-3-methoxybenzylsulfonamido)thioacetamide;
(N-ethyl-2,3-di-trifluoromethylbenzylsulfonamido)thioacetamide;
(N-ethyl-2,4-di-trifluoromethylbenzylsulfonamido)thioacetamide;
(N-ethyl-2,5-di-trifluoromethylbenzylsulfonamido)thioacetamide;
(N-ethyl-3-chloro-5-trifluoromethylbenzylsulfonamido)acetate;
(N-ethyl-3,4-dichlorobenzylsulfonamido)thioacetamide;
(N-ethyl-2-chloro-6-trifluoromethyl-benzylsulfonamido)thioacetamide;
(N-ethyl-2-butyl-3-chlorobenzylsulfonamido)thioacetamide;
(N-ethyl-2-chloro-4-trifluoromethylbenzylsulfonamido)thioacetamide;
(N-ethyl-2-chloro-3-bromobenzylsulfonamido)thioacetamide;
(N-ethyl-3-chloro-5-methylbenzylsulfonamido)thioacetamide;
(N-ethyl-2,4,5-trifluorobenzylsulfonamido)thioacetamide;
(N-ethyl-pentafluorophenylmethylsulfonamido)thioacetamide;
(N-propyl-3-trifluoromethylbenzylsulfonamido)thioacetamide;
(N-isopropyl-3-difluoromethylbenzylsulfonamido)thioacetamide;
(N-pentyl-3-ethylbenzylsulfonamido)thioacetamide;
(N-cyclopropyl-3-t-butylbenzylsulfonamido)thioacetamide;
(N-hexyl-3-ethoxybenzylsulfonamido)thioacetamide;
(N-propyl-2-chlorobenzylsulfonamido)thioacetamide;
(N-butyl-3-methoxybenzylsulfonamido)thioacetamide;
(N-pentyl-3-fluorobenzylsulfonamido)thioacetamide;
(N-hexyl-3-bromobenzylsulfonamido)thioacetamide;
(N-cyclohexyl-3-nitrobenzylsulfonamido)thioacetamide;
(N-cyclopropyl-2,5-di-trifluoromethylbenzylsulfonamido)thioacetamide;
(N-propyl-3-chloro-4-methoxybenzylsulfonamido)thioacetamide;
(N-isopropyl-2-chloro-6-methoxybenzylsulfonamido)thioacetamide;
(N-butyl-2,3-dichloro-6-trifluoromethylbenzylsulfonamido)thioacetamide;
(N-isopropyl-2-chloro-4-trifluoromethylbenzylsulfonamido)thioacetamide;
(N-pentyl-2-fluoro-3-chlorobenzylsulfonamido)thioacetamide;
(N-hexyl-2-fluoro,3,4-dibromobenzylsulfonamido)thioacetamide.

Example 11

(N-Allyl-3-Trifluoromethylbenzylsulfonamido)thioacetamide

This title compound can be prepared via the following procedure.

3.12 g of 3-trifluoromethylbenzylsulfonamidothioacetamide is dissolved in 10 ml of dry dimethylformamide. To this ice-cooled solution is added 0.24 g of sodium hydride. The reaction mixture is stirred for 15 minutes at room temperature and then 0.95 ml of allyl bromide dissolved in 5 ml of dimethylformamide is added dropwise. After about 30 minutes, the reaction mixture is diluted with 150 ml of water and extracted twice with 75 ml portions of diethyl ether. Petroleum ether is added to the combined ether phases then washed with 100 ml of water. The title compound can be recovered from this mixture by appropriate recovery procedures over magnesium sulfate and stripped to a white solid.

Similarly by adapting the general procedure used above using the appropriate starting materials the following compounds can be prepared:
(N-allyl-3-difluoromethylbenzylsulfonamido)thioacetamide;
(N-allyl-3-ethylbenzylsulfonamido)thioacetamide;
(N-allyl-3-t-butylbenzylsulfonamido)thioacetamide;
(N-allyl-3-chlorobenzylsulfonamido)thioacetamide;
(N-allyl-3-ethoxybenzylsulfonamido)thioacetamide;
(N-allyl-3-butylbenzylsulfonamido)thioacetamide;
(N-allyl-2-trifluoromethylbenzylsulfonamido)thioacetamide;
(N-allyl-3-2',2'-difluoroethylbenzylsulfonamido)thioacetamide;
(N-allyl-2,3,6-trichlorobenzylsulfonamido)thioacetamide;
(N-allyl-3-methoxybenzylsulfonamido)thioacetamide;
(N-allyl-3-fluorobenzylsulfonamido)thioacetamide;
(N-allyl-3-bromobenzylsulfonamido)thioacetamide;
(N-allyl-3-nitrobenzylsulfonamido)thioacetamide;
(N-allyl-3-proxybenzylsulfonamido)thioacetamide;
(N-allyl-2,5-di-trifluoromethylbenzylsulfonamido)thioacetamide;
(N-allyl-3-trifluoromethyl-5-bromobenzylsulfonamido)thioacetamide;
(N-allyl-3,4-ditrifluoromethylbenzylsulfonamido)thioacetamide;
(N-allyl-2,6-dichlorobenzylsulfonamido)thioacetamide;
(N-allyl-2-chloro-3-methylbenzylsulfonamido)thioacetamide;
(N-allyl-2-chloro-4-trifluoromethylbenzylsulfonamido)thioacetamide;
(N-allyl-2-chloro-3-bromobenzylsulfonamido)thioacetamide;

(N-allyl-2-chloro-4-1′,2′,2′trifluoroethylbenzylsulfonamido)thioacetamide;
(N-allyl-3-fluoromethylbenzylsulfonamido)thioacetamide;
(N-allyl-3-nitrobenzylsulfonamido)thioacetamide;
(N-allyl-3-trifluoromethyl-5-methoxybenzylsulfonamido)thioacetamide;
(N-allyl-3-trifluoromethyl-4-chlorobenzylsulfonamido)thioacetamide;
(N-allyl-2,3,5,6-tetrafluorobenzylsulfonamido)thioacetamide;
(N-propyl-3-trifluoromethylbenzylsulfonamido)thioacetamide;
(N-butyl-3-difluoromethylbenzylsulfonamido)thioacetamide;
(N-pentyl-3-ethylbenzylsulfonamido)thioacetamide;
(N-hexyl-3-ethylbenzylsulfonamido)thioacetamide;
(N-pentyl-2-chlorobenzylsulfonamido)thioacetamide;
(N-hexyl-3-bromobenzylsulfonamido)thioacetamide;
(N-propyl-3,4-di-trifluoromethylbenzylsulfonamido)thioacetamide;
(N-isopropyl-2,6-dichlorobenzylsulfonamido)thioacetamide;
(N-butyl-2-chloro-3-methylbenzylsulfonamido)thioacetamide;
(N-hexyl-2-chloro-4-trifluoromethylbenzylsulfonamido)thioacetamide;
(N-pentyl-2-chloro-3-bromobenzylsulfonamido)thioacetamide;
(N-hexyl-2-bromo-3-trifluoromethylbenzylsulfonamido)thioacetamide;
(N-cyanomethyl-3-trifluoromethylbenzylsulfonamido)thioacetamide;
(N-cyanomethyl-3-iodobenzylsulfonamido)thioacetamide;
(N-cyanomethyl-3-fluoromethylbenzylsulfonamido)thioacetamide;
(N-cyanomethyl-3-difluoromethylbenzylsulfonamido)thioacetamide;
(N-cyanomethyl-3-ethylbenzylsulfonamido)thioacetamide;
(N-cyanomethyl-3-t-butylbenzylsulfonamido)thioacetamide;
(N-cyanomethyl-3-n-butylbenzylsulfonamido)thioacetamide;
(N-cyanomethyl-3-ethoxybenzylsulfonamido)thioacetamide;
(N-cyanomethyl-2-trifluoromethylbenzylsulfonamido)thioacetamide;
(N-cyanomethyl-2-chlorobenzylsulfonamido)thioacetamide;
(N-cyanomethyl-2-pentafluorobenzylsulfonamido)thioacetamide;
(N-cyanomethyl-3-pentylbenzylsulfonamido)thioacetamide;
(N-cyanomethyl-3-methoxybenzylsulfonamido)thioacetamide;
(N-cyanomethyl-3-fluorobenzylsulfonamido)thioacetamide;
(N-cyanomethyl-3-bromobenzylsulfonamido)thioacetamide;
(N-cyanomethyl-3-nitrobenzylsulfonamido)thioacetamide;
(N-cyanomethyl-3-difluoromethylbenzylsulfonamido)acetamide;
(N-cyanomethyl-3-propoxybenzylsulfonamido)thioacetamide;
(N-cyanomethyl-2,6-di-trifluoromethylbenzylsulfonamido)thioacetamide;
(N-cyanomethyl-2,5-di-trifluoromethylbenzylsulfonamido)thioacetamide;
(N-cyanomethyl-3,5-di-difluoromethylbenzylsulfonamido)thioacetamide;
(N-cyanomethyl-3-chloro-4-methoxybenzylsulfonamido)thioacetamide;
(N-cyanomethyl-2-chloro-6-methoxybenzylsulfonamido)thioacetamide;
(N-cyanomethyl-3-chloro-5-bromobenzylsulfonamido)thioacetamide;
(N-cyanomethyl-2,6-dichlorobenzylsulfonamido)thioacetamide;
(N-cyanomethyl-2-iodo-3-chlorobenzylsulfonamido)thioacetamide;
(N-cyanomethyl-2-chloro-4-trifluoromethylbenzylsulfonamido)thioacetamide;
(N-cyanomethyl-2-fluoro-3-chlorobenzylsulfonamido)thioacetamide;
(N-cyanomethyl-2-ethyl-3-trifluoromethylbenzylsulfonamido)thioacetamide;
(N-cyanomethyl-3-trifluoromethyl-5-iodobenzylsulfonamido)thioacetamide;
(N-cyanomethyl-4-chloro-3-trifluoromethylbenzylsulfonamido)thioacetamide;
(N-cyanomethyl-2-chloro-4-4′,4′-difluorobutylbenzylsulfonamido)thioacetamide;
(N-cyanomethyl-2,4,5-trifluorobenzylsulfonamido)thioacetamide;
(N-methoxymethyl-3-trifluoromethylbenzylsulfonamido)thioacetamide;
(N-1′-methoxyethyl-3-trifluoromethylbenzylsulfonamido)thioacetamide;
(N-3′-propoxypropyl-3-trifluoromethylbenzylsulfonamido)thioacetamide;
(N-2′,3′-epoxypropyl-3-trifluoromethylbenzylsulfonamido)thioacetamide;
(N-3′,4′-epoxypentyl-3-trifluoromethylbenzylsulfonamido)thioacetamide;
(N-methylthiomethyl-3-trifluoromethylbenzylsulfonamido)thioacetamide;
(N-2′-ethylthiopropyl-3-trifluoromethylbenzylsulfonamido)thioacetamide;
(N-hex-4-enyl-3-trifluoromethylbenzylsulfonamido)thioacetamide;
(N-2′-hydroxyethyl-3-trifluoromethylbenzylsulfonamido)thioacetamide;
(N-2′,2′-dichloroethyl-3-trifluoromethylbenzylsulfonamido)thioacetamide;
(N-2′,3′-epoxypropyl-3-ethylbenzylsulfonamido)thioacetamide;
(N-5′,6′-epoxyhexyl-3-t-butylbenzylsulfonamido)thioacetamide;
(N-2′,2′-dichloroethyl-3-ethoxybenzylsulfonamido)thioacetamide;
(N-isopropylthiomethyl-2-trifluoromethylbenzylsulfonamido)thioacetamide;
(N-6′-methylthiohexyl-2-chlorobenzylsulfonamido)thioacetamide;
(N-methoxymethyl-2-2′,3′-difluoropropylbenzylsulfonamido)thioacetamide;
N-2′-methoxyethyl-3-fluorobenzylsulfonamido)thioacetamide;
(N-2′-propoxypropyl-3-methoxybenzylsulfonamido)thioacetamide;
(N-2′,3′-epoxypropyl-3-fluorobenzylsulfonamido)thioacetamide;

(N-3',4'-epoxybutyl-3-bromobenzylsulfonamido)thioacetamide;
(N-3'-hydroxypropyl-3-nitrobenzylsulfonamido)thioacetamide;
(N-pentylthiomethyl-3,5-di-trifluoromethylbenzylsulfonamido)thioacetamide;
(N-2'-propylthiobutyl-2,5-di-trifluoromethylbenzylsulfonamido)thioacetamide;
(N-pent-2-enyl-3,5-di-difluoromethylbenzylsulfonamido)thioacetamide;
(N-4'-hydroxybutyl-3-chloro-4-methoxybenzylsulfonamido)thioacetamide;
(N-cyclopentyl-3-chlorobenzylsulfonamido)thioacetamide;
(N-2'-hydroxyethyl-3-chlorobenzylsulfonamido)thioacetamide;
(N-isopropylthiomethyl-2-chloro-4-trifluoromethylbenzylsulfonamido)thioacetamide;
(N-2'-methylthiopropyl-2-chloro-3-bromobenzylsulfonamido)thioacetamide;
(N-pentoxymethyl-3-nitrobenzylsulfonamido)thioacetamide;
(N-3'-butoxypropyl-3-trifluoromethylbenzylsulfonamido)thioacetamide;
(N-isopropoxymethyl-3-difluoromethylbenzylsulfonamido)thioacetamide.

EXAMPLE 12

Sodium Salt of (N-ethyl-3-trifluoromethylbenzylsulfonamido)acetamide

In this example, 1.5 g of (N-ethyl-3-trifluoromethylbenzylsulfonamido)acetamide was suspended in 30 ml of dry tetrahydrofuran. To this suspension was added 0.11 g of sodium hydride. Reaction was essentially instantaneous. The solvent was stripped to a solid which was triturated with ether to afford 1.5 g of the title compound. This material is very hygroscopic and turns into an oil upon standing.

Similarly, by applying this procedure to the compound of Examples 2, 3, 4, 78, 10 and 11 the corresponding sodium salts can be prepared.

EXAMPLE 13

In this example, the compounds of the invention and the comparison compounds listed in the following tables were respectively tested using the procedures described hereinbelow for pre-emergent and post-emergent activity against a variety of grasses and broad-leaf plants including one grain crop and one broad-leaf crop. The compounds tested are identified by compound number in the Table A hereinbelow.

Pre-Emergent Herbicide Test

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface at a dose of 27.5 micrograms/cm$^2$ unless otherwise specified in the following Tables. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm$^2$ unless otherwise specified in the following Tables. After the plants had dried, they were placed in a greenhouse and then watered intermittently at their bases as needed. The plants were observed periodically for phytotoxic effects and physiological and morphologically responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE A $$ArCH_2SO_2\overset{R}{N}-CH_2\overset{\overset{X}{\|}}{C}NHR^a$$

| No. | Ar | R | R$^a$ | X | Melting Point °C. |
|---|---|---|---|---|---|
| 1 | 3-CF$_3\phi$— | CH$_3$ | H | O = | 163–164 |
| 2 | 3-CF$_3\phi$— | CH$_3$CH$_2$— | H | O = | 122–123 |
| 3 | 3-CF$_3\phi$— | CH$_2$=CHCH$_2$— | H | O = | 91–92 |
| 4 | 3-CF$_3\phi$— | CH≡CCH$_2$— | H | O = | 87–88 |
| 5 | 3-CF$_3\phi$— | cyclopropyl | H | O = | 143.5–145 |
| 6 | 3-CF$_3\phi$— | cyclopentyl | H | O = | 131–132.5 |
| 7 | 3-CF$_3\phi$— | CH$_2$—cyclopropyl | H | O = | 110 |
| 8 | 3-CF$_3\phi$— | CH$_3$OCH$_2$— | H | O = | 105–108 |
| 9 | 3-CF$_3\phi$— | CH$_3$OCH$_2$CH$_2$— | H | O = | 128–129 |
| 10 | 3-CF$_3\phi$— | CF$_3$CH$_2$— | H | O = | 143.5–145 |
| 11 | 3-CF$_3\phi$— | FCH$_2$CH$_2$— | H | O = | 94–98 |
| 12 | 3-CF$_3\phi$— | ClCH$_2$CH$_2$— | H | O = | 111–112 |
| 13 | 3-CF$_3\phi$— | CH$_3$— | OH— | O = | 128–129 |
| 14 | 3-CF$_3\phi$— | CH$_3$— | CH$_3$C(O)— | O = | 137.5–138 |

* = Decomposition
$\phi$** = Phenyl, for example, 2-Cl$\phi$ = 2-chlorophenyl

TABLE A-continued $$\text{ArCH}_2\text{SO}_2\overset{R}{\underset{|}{N}}-\text{CH}_2\overset{X}{\underset{||}{C}}\text{NHR}^a$$

| | | | | | |
|---|---|---|---|---|---|
| 15 | 3-CF$_3\phi$— | CH$_3$CH$_2$— | CH$_3$C(O) | O = | 97–98 |
| 16 | 3-CF$_3\phi$— | CH$_3$CH$_2$— | CH$_3$CH$_2$CH$_2$C(O)— | O = | 99.5–100.5 |
| 17 | 3-Cl$\phi$— | CH$_3$— | H | O = | 151–166 |
| 18 | 2-F—5-CF$_3\phi$— | CH$_3$CH$_2$— | H | O = | 134–135 |
| 19 | 2-F—5-CF$_3\phi$— | CH$_3$CH$_2$— | H | O = | 152.2 |
| 20 | 2-Cl—5-CF$_3\phi$— | CH$_3$— | H | O = | 171–177 |
| 21 | 2-Cl—5-CF$_3\phi$— | CH$_3$CH$_2$— | H | O = | 135–138 |
| 22 | 2-Br—5CF$_3\phi$— | CH$_3$— | H | O = | 184–186 |
| 23 | 3,5-di(CF$_3$)$\phi$ | CH$_3$— | H | O = | 145–150 |
| 24 | 3,5-di(Cl)$\phi$— | CH$_3$— | H | O = | 155–162 |
| 25 | 2,5-di(Cl)$\phi$— | CH$_3$— | H | O = | 202–206 |
| 26 | 3,5-di(Cl)$\phi$— | CH$_3$CH$_2$— | H | O = | 150–154 |
| 27 | 2-NO$_2$—5-Cl$\phi$— | CH$_3$CH$_2$— | H | O = | 173–174 |

*2-F—5-CF$_3\phi$— = 2-fluoro-5 trifluoromethylphenyl

| | | | | | |
|---|---|---|---|---|---|
| 28 | 2-Cl—5-NO$_2\phi$— | CH$_3$CH$_2$— | H | O = | 180–181 |
| 29 | 2,3,6-tri(Cl)$\phi$— | CH$_3$— | H | O = | 172–183 |
| 30 | 2,3,6-tri(Cl)$\phi$— | CH$_3$CH$_2$— | H | O = | 110–120 |
| 31 | 2,3-di(Cl)—5-CF$_3\phi$— | CH$_3$CH$_2$— | H | O = | 156 |
| 32 | 3-CF$_3\phi$— | CH$_3$ | H | S = | 173–175 |
| 33 | 3-Cl | CH$_3$ | H | S = | 183–184 |
| 34 | 3-CF$_3\phi$— | CH$_3$CH$_2$— | H | S = | 158–160 |
| 35 | 3-Cl$\phi$— | CH$_3$CH$_2$— | H | S = | 148–149 |
| 36 | 3-CF$_3\phi$— | CH$_3$=CHCH$_2$— | H | S = | 141–142.5 |
| 37 | 3-CF$_3\phi$— | CH≡CCH$_2$— | H | S = | 142–143 |
| 38 | 2-Cl—5-CF$_3\phi$— | CH$_3$CH$_2$— | H | S = | 163–165.5 |
| 39 | 2,3-di(Cl)—5-CF$_3\phi$— | CH$_3$CH$_2$— | H = | S = | 139.5–143 |

TABLE C

COMPARISON COMPOUNDS $$\text{Ar}-\text{A}-\text{SO}_2\overset{R}{\underset{|}{N}}-\text{CH}_2-\overset{X}{\underset{||}{C}}\text{NHR}^1\text{R}^a$$

| No. | Ar | R | R$^1$ | R$^a$ | A | X | Melting Point °C. |
|---|---|---|---|---|---|---|---|
| C-1 | 3-CF$_3\phi$— | CH$_3$ | H | H | *— | O = | 179–180 |
| C-2 | 3-CF$_3\phi$— | CH$_3$ | H | H | —CH(CH$_3$)— | O = | 122–124 |
| C-3 | 3-CF$_3\phi$— | CH$_3$ | H | H | —C(CH$_3$)$_2$— | O = | 144–146 |
| C-4 | 3-CF$_3\phi$— | CH$_3$CH$_2$ | CH$_3$ | H | —CH$_2$— | O = | 111–112.5 |
| C-5 | 3-CF$_3\phi$— | CH$_3$ | CH$_3$ | CH$_3$ | —CH$_2$— | O = | 90–92 |
| C-6 | 3-CF$_3\phi$— | CH$_3$ | CH$_3$O— | H | —CH$_2$— | O = | 154–155 |
| C-7 | 3-CF$_3\phi$— | CH$_3$ | NH$_2$— | H | —CH$_2$— | O = | 135 |
| C-8 | 3-CF$_3\phi$— | CH$_3$ | phenyl | H | —CH$_2$— | O = | 158–160 |
| C-9** | 3-CF$_3\phi$— | H | H | H | —CH$_2$— | O = | 147–149 |
| C-10 | 3-CF$_3\phi$— | CH$_3$OC(O)— | H | H | —CH$_2$— | O = | 154–158 |
| C-11 | 3-CF$_3\phi$— | HO—C$_2$H$_5$— | H | H | —CH$_2$ | O = | 173–174.5 |
| C-12 | 2-NO$_2\phi$— | CH$_3$ | H | H | —CH$_2$— | O = | 135.6 |
| C-13 | 3,5-di(NO$_2$)$\phi$ | CH$_3$CH$_2$ | H | H | —CH$_2$— | O = | 166–172 |

*Direct attachment of phenyl to sulfonyl
**Intermediate

TABLE 1

Pre-Emergence Herbicidal Activity
Application Rate: 27.5 micrograms/cm$^2$, unless otherwise noted

| Compound No. | Broad-Leaf Plants % Phototoxicity | | | | Grasses % Phototoxicity | | | |
|---|---|---|---|---|---|---|---|---|
| | Lambsquarter | Mustard | Pigweed | Soybean | Barnyardgrass | Crabgrass | Wild Oats | Rice |
| 1 | 0 | 0 | 0 | 0 | 100 | 0 | 0 | 0 |
| 2 | 0 | 0 | 0 | 0 | 100 | 0 | 0 | 0 |
| 3 | 0 | 0 | 0 | 0 | 100 | 0 | 0 | 0 |
| 4 | 0 | 0 | 0 | 0 | 100 | 0 | 0 | 0 |
| 5 | 0 | 0 | 0 | 0 | 100 | 0 | 0 | 0 |
| 6 | 0 | 0 | 0 | 0 | 95 | 0 | 0 | 0 |
| 7 | 0 | 0 | 0 | 0 | 100 | 0 | 0 | 0 |
| 8 | 0 | 0 | 0 | 0 | 100 | 0 | 0 | 0 |
| 9 | 0 | 0 | 0 | 0 | 100 | 0 | 0 | 0 |
| 10 | 0 | 0 | 0 | 0 | 100 | 0 | 0 | 0 |
| 11 | 0 | 0 | 0 | 0 | 100 | 0 | 0 | 0 |
| 12 | 0 | 0 | 0 | 0 | 100 | 0 | 0 | 0 |
| 13 | 0 | 0 | 0 | 0 | 100 | 0 | 0 | 0 |
| 14 | 0 | 0 | 0 | 0 | 100 | 0 | 0 | 0 |
| 15 | 0 | 0 | 0 | 0 | 100 | 0 | 0 | 0 |
| 16 | 0 | 0 | 0 | 0 | 100 | 0 | 0 | 0 |

TABLE 1-continued

Pre-Emergence Herbicidal Activity
Application Rate: 27.5 micrograms/cm², unless otherwise noted

| Compound No. | Broad-Leaf Plants % Phototoxicity | | | | Grasses % Phototoxicity | | | |
|---|---|---|---|---|---|---|---|---|
| | Lambsquarter | Mustard | Pigweed | Soybean | Barnyardgrass | Crabgrass | Wild Oats | Rice |
| 17 | 0 | 0 | 0 | 0 | 100 | 0 | 0 | 0 |
| 18 | 0 | 0 | 0 | 0 | 100 | 0 | 0 | 0 |
| 19 | 0 | 0 | 0 | 0 | 100 | 0 | 0 | 0 |
| 20 | 0 | 0 | 0 | 0 | 100 | 0 | 0 | 0 |
| 21 | 30 | 0 | 70 | 0 | 100 | 0 | 10 | 0 |
| 22 | 0 | 0 | 0 | 0 | 100 | 0 | 0 | 0 |
| 23 | 0 | 0 | 0 | 0 | 100 | 0 | 0 | 0 |
| 24 | 0 | 0 | 0 | 0 | 100 | 0 | 0 | 0 |
| 25 | 0 | 0 | 0 | 0 | 100 | 0 | 0 | 0 |
| 26 | 0 | 0 | 0 | 0 | 100 | 0 | 0 | 0 |
| 27 | 0 | 0 | 0 | 0 | 100 | 0 | 0 | 0 |
| 28 | 0 | 0 | 0 | 0 | 100 | 0 | 0 | 0 |
| 29 | 0 | 0 | 0 | 30 | 100 | 0 | 0 | 0 |
| 30 | 0 | 0 | 0 | 0 | 100 | 0 | 0 | 0 |
| 31 | 90 | 0 | 70 | 0 | 100 | 0 | 0 | 0 |
| 32 | 0 | 0 | 0 | 0 | 100 | 0 | 0 | 0 |
| 33 | 0 | 0 | 0 | 0 | 100 | 0 | 0 | 0 |
| 34 | 0 | 0 | 0 | 0 | 100 | 0 | 0 | 0 |
| 35 | 0 | 0 | 0 | 0 | 100 | 0 | 0 | 0 |
| 36 | 0 | 0 | 0 | 0 | 100 | 0 | 0 | 0 |
| 37 | 0 | 0 | 0 | 0 | 100 | 0 | 0 | 0 |
| 38 | 0 | 0 | 0 | 0 | 100 | 0 | 0 | 0 |
| 39 | 90 | 0 | 90 | 0 | 100 | 0 | 0 | 0 |

TABLE 1A

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Barnyardgrass | Crabgrass | Wild Oats | Rice |
| C-1 | 0 | 0 | 0 | 0 | 0 | 0 | 0 | 0 |
| C-2 | 0 | 0 | 0 | 0 | 30 | 0 | 0 | 0 |
| C-3 | 0 | 0 | 0 | 0 | 0 | 0 | 0 | 0 |
| C-4 | 0 | 0 | 0 | 0 | 25 | 0 | 0 | 0 |
| C-5 | 0 | 0 | 0 | 0 | 85 | 0 | 0 | 0 |
| C-6 | 0 | 0 | 0 | 0 | 70 | 0 | 0 | 0 |
| C-7 | 0 | 0 | 0 | 0 | 20 | 0 | 0 | 0 |
| C-8 | 0 | 0 | 0 | 0 | 25 | 0 | 0 | 0 |
| C-9 | 0 | 0 | 0 | 0 | 0 | 0 | 0 | 0 |
| C-10 | 0 | 0 | 0 | 0 | 0 | 0 | 0 | 0 |
| C-11 | 0 | 0 | 0 | 0 | 50 | 0 | 0 | 0 |
| C-12 | 0 | 0 | 0 | 0 | 0 | 0 | 0 | 0 |
| C-13 | 0 | 0 | 0 | 0 | 0 | 0 | 0 | 0 |

TABLE 2

Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Barnyardgrass | Crabgrass | Wild Oats | Rice |
| 1 | 0 | 0 | 0 | 0 | 80 | 0 | 0 | 0 |
| 2 | 0 | 0 | 0 | 0 | 100 | 0 | 0 | 0 |
| 3 | 0 | 0 | 0 | 0 | 100 | 0 | 0 | 0 |
| 4 | 0 | 0 | 0 | 0 | N.T. | 0 | 0 | 0 |
| 5 | 0 | 0 | 0 | 0 | N.T. | 0 | 0 | 0 |
| 6 | 0 | 0 | 0 | 0 | N.T. | 0 | 0 | 0 |
| 7 | 0 | 0 | 0 | 0 | 100 | 0 | 0 | 0 |
| 8 | 0 | 0 | 0 | 0 | N.T. | 0 | 0 | 0 |
| 9 | 0 | 0 | 0 | 0 | 100 | 0 | 0 | 0 |
| 10 | 0 | 0 | 0 | 0 | N.T. | 0 | 0 | 0 |
| 11 | 0 | 0 | 0 | 0 | 100 | 0 | 0 | 0 |
| 12 | 0 | 0 | 0 | 0 | 100 | 0 | 0 | 0 |
| 13 | 0 | 0 | 0 | 0 | 100 | 0 | 0 | 0 |
| 14 | 0 | 0 | 0 | 0 | 99 | 0 | 0 | 0 |
| 15 | 0 | 0 | 0 | 0 | 100 | 0 | 0 | 0 |
| 16 | 0 | 0 | 0 | 0 | 100 | 0 | 0 | 0 |
| 17 | 0 | 0 | 0 | 0 | 98 | 0 | 0 | 0 |
| 18 | 0 | 0 | 0 | 0 | 100 | 0 | 0 | 0 |
| 19 | 0 | 0 | 0 | 0 | 100 | 0 | 0 | 0 |
| 20 | 0 | 0 | 0 | 0 | 100 | 0 | 0 | 0 |
| 21 | 0 | 0 | 0 | 0 | 100 | 0 | 0 | 0 |
| 22 | 0 | 0 | 0 | 0 | 85 | 0 | 0 | 0 |
| 23 | 0 | 0 | 0 | 0 | 100 | 0 | 0 | 0 |

TABLE 2-continued

Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Barnyardgrass | Crabgrass | Wild Oats | Rice |
| 24 | 0 | 0 | 0 | 0 | 100 | 0 | 0 | 0 |
| 25 | 0 | 0 | 0 | 0 | 100 | 0 | 0 | 0 |
| 26 | 0 | 0 | 0 | 0 | 90 | 0 | 0 | 0 |
| 27 | 0 | 0 | 0 | 0 | 100 | 0 | 0 | 0 |
| 28 | 0 | 0 | 0 | 0 | 100 | 0 | 0 | 0 |
| 29 | 20 | 20 | 0 | 30 | 100 | 0 | 0 | 0 |
| 30 | 0 | 0 | 0 | 30 | 100 | 0 | 0 | 0 |
| 31 | 0 | 0 | 0 | 0 | 100 | 0 | 0 | 0 |
| 32 | 0 | 0 | 0 | 0 | 100 | 0 | 0 | 0 |
| 33 | 0 | 0 | 0 | 0 | 100 | 0 | 0 | 0 |
| 34 | 0 | 0 | 0 | 0 | 100 | 0 | 0 | 0 |
| 35 | 0 | 0 | 0 | 0 | 100 | 0 | 0 | 0 |
| 36 | 0 | 0 | 0 | 0 | 100 | 0 | 0 | 0 |
| 37 | 0 | 0 | 0 | 0 | 100 | 0 | 0 | 0 |
| 38 | 0 | 0 | 0 | 0 | 100 | 0 | 0 | 0 |
| 39 | 0 | 0 | 0 | 0 | 100 | 0 | 0 | 0 |

N.T. = Not Tested

TABLE 2A

COMPARISON COMPOUNDS
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Barnyardgrass | Crabgrass | Wild Oats | Rice |
| C-1 | 0 | 0 | 0 | 0 | 0 | 0 | 0 | 0 |
| C-2 | 0 | 0 | 0 | 0 | 0 | 0 | 0 | 0 |
| C-3 | 0 | 0 | 0 | 0 | 100 | 40 | 40 | 30 |
| C-4 | 0 | 0 | 0 | 0 | 0 | 0 | 0 | 0 |
| C-5 | 0 | 0 | 0 | 0 | 0 | 0 | 0 | 0 |
| C-6 | 0 | 0 | 0 | 0 | 80 | 0 | 0 | 0 |
| C-7 | 0 | 0 | 0 | 0 | 0 | 0 | 0 | 0 |
| C-8 | 0 | 0 | 0 | 0 | 15 | 0 | 0 | 0 |
| C-9 | 0 | 0 | 0 | 0 | 0 | 0 | 0 | 0 |
| C-10 | 0 | 0 | 0 | 0 | 0 | 0 | 0 | 0 |
| C-11 | 0 | 0 | 0 | 0 | 50 | 0 | 0 | 0 |
| C-12 | 0 | 0 | 0 | 0 | 0 | 0 | 0 | 0 |
| C-13 | 0 | 0 | 0 | 0 | 0 | 0 | 0 | 0 |

As can be seen from the above Tables, the herbicides of the invention exhibited excellent selective pre and post-emergence phytotoxicity against barnyardgrass. Whereas, the closely related comparison compounds were much less active and in most cases were wholly inactive. Moreover, the compounds of the invention did not exhibit any pre or post-emergence phytotoxicity with respect to rice.

Obviously, many modifications and variations of the invention described hereinabove and below can be made without departing from the essence and scope thereof.

What is claimed is:

1. A compound having the formula:

$$ArCH_2SO_2\overset{R}{\underset{|}{N}}-CH_2-\overset{X}{\underset{||}{C}}NHR^1 \quad (Ix)$$

wherein
X is O= or S=;
R is lower alkyl having 1 through 6 carbon atoms; cycloalkyl having 3 through 6 carbon atoms; (cycloalkyl)alkyl having 3 through 6 carbon atoms in the cycloalkyl moiety and 1 through 3 carbon atoms in the alkyl moiety; lower alkenyl having 2 through 6 carbon atoms; lower alkynyl having 2 through 6 carbon atoms; 3-iodopropargyl; alkanoyl having 2 through 6 carbon atoms; alkoxyalkyl wherein the alkoxy and alkyl moieties independently have 1 through 6 carbon atoms; alkylthioalkyl wherein the alkyl moieties thereof independently have 1 through 6 carbon atoms; epoxyalkylmethylene having 3 through 6 carbon atoms; haloalkylmethyl having 2 through 4 carbon atoms and 1 through 4 halo atoms independently selected from the group of fluoro, chloro and bromo; or cyanomethyl;

$R^1$ is hydrogen; alkanoyl having 2 through 5 carbon atoms; or hydroxy; with the proviso that when X is S=, then $R^1$ is hydrogen;

Ar is substituted phenyl selected from the group of tetrafluorophenyl; pentafluorophenyl; trisubstituted phenyls having three substituents independently selected from the group of fluoro, chloro, bromo and trifluoromethyl; and substituted phenyls having the formulas

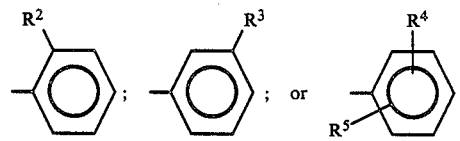

wherein $R^2$ is methyl, trifluoromethyl or chloro;

R³ is halo, alkyl having 1 through 4 carbon atoms, alkoxy having 1 through 4 carbon atoms, fluoroalkyl having 1 through 4 fluoro atoms and 1 through 4 carbon atoms or nitro; one of R⁴ or R⁵ is trifluoromethyl or chloro and the other is halo, nitro, alkyl having 1 through 4 carbon atoms, alkoxy having 1 through 4 carbon atoms, or fluoroalkyl having 1 through 4 fluoro atoms and 1 through 4 carbon atoms;

and hydrates and compatible salts of the compounds of formula (IX).

2. The compound of claim 1 of Formula (IX), and compatible salts and hydrates thereof, wherein R is alkyl having 1 through 4 carbon atoms; cycloalkyl; (cyclopropyl)methyl; alkenyl having 2 through 4 carbon atoms; lower alkynyl having 3 or 4 carbon atoms; 3-iodopropargyl; alkanoyl having 2 through 4 carbon atomns; alkoxyalkyl wherein the alkoxy and alkyl moieties independently have 1 through 4 carbon atoms; alkylthioalkyl wherein the alkyl moieties independently having 1 through 4 carbon atoms; epoxyalkylmethylene; haloalkylmethyl or cyanomethyl; and Ar is selected from the group of tetrafluorophenyl, pentafluorophenyl, trisubstituted phenyl having three substituents independently selected from the group of chloro, bromo, and trifluoromethyl; and substituted phenyls having the formula

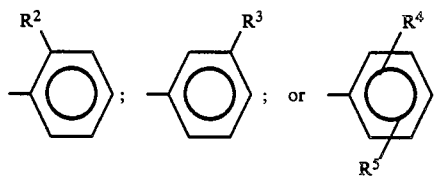

wherein R² is methyl trifluoromethyl or chloro;
R³ is halo or trifluoromethyl;
one of R⁴ or R⁵ is trifluoromethyl or chloro and the other is trifluoromethyl or halo.

3. A compound having the formula:

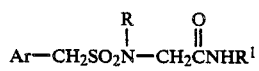

wherein
R is a lower alkyl having 1 through 6 carbon atoms; cycloalkyl having 3 through 6 carbon atoms; (cycloalkyl)alkyl having 3 through 6 carbon atoms in the cycloalkyl moiety and 1 through 3 carbon atoms in the alkyl moiety; lower alkenyl having 2 through 6 carbon atoms; lower alkynyl having 2 through 6 carbon atoms; 3-iodopropargyl; alkanoyl having 2 through 6 carbon atoms; alkoxyalkyl wherein the alkoxy and alkyl moieties independently have 1 through 6 carbon atoms; alkylthioalkyl wherein the alkyl moieties thereof independently have 1 through 6 carbon atoms; epoxyalkylmethylene having 3 through 6 carbon atoms; haloalkylmethyl having 2 through 4 carbon atoms and 1 through 4 halo atoms independently selected from the group of fluoro, chloro and bromo; or cyanomethyl;

R¹ is hydrogen, alkanoyl having 2 through 5 carbon atoms; or hydroxy;

Ar is substituted phenyl selected from the group of tetrafluorophenyl; pentafluorophenyl; trisubstituted phenyls having three substituents independently selected from the group of fluoro, chloro, bromo and trifluoromethyl; and substituted phenyls having the formulas

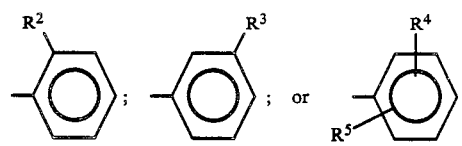

wherein R² is methyl, trifluoromethyl or chloro;
R³ is halo, alkyl having 1 through 4 carbon atoms, alkoxy having 1 through 4 carbon atoms, fluoroalkyl having 1 through 4 fluoro atoms and 1 through 4 carbon atoms or nitro; one of R⁴ or R⁵ is trifluoromethyl or chloro and the other is halo, nitro, alkyl having 1 through 4 carbon atoms, alkoxy having 1 through 4 carbon atoms, or fluoroalkyl having 1 through 4 fluoro atoms and 1 through 4 carbon atoms;

and hydrates and compatible salts thereof.

4. The compound of claim 3, having the formula

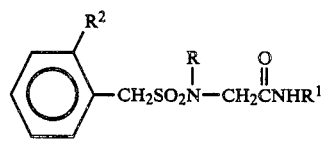

wherein R, R¹ and R² are as defined in claim 3; and hydrates and compatible salts thereof.

5. The compound of claim 4 wherein R is methyl, ethyl, propyl, cyclopropyl, allyl, 2-propynyl, 3-iodopropargyl, methoxymethyl, 2-fluoroethyl or 2,2,2-trifluoroethyl and R¹ is hydrogen.

6. The compound of claim 5 wherein R is methyl, ethyl, 2-propynyl, 2-fluoroethyl or 2,2,2-trifluoroethyl.

7. The compound of claim 4 wherein R¹ is hydrogen.

8. The compound of claim 4 wherein R² is trifluoromethyl.

9. The compound of claim 6 wherein R² is trifluoromethyl.

10. The compound of claim 9 wherein R is ethyl.

11. The compound of claim 4 wherein R¹ is alkanoyl or hydroxy.

12. The compound of claim 3 having the formula

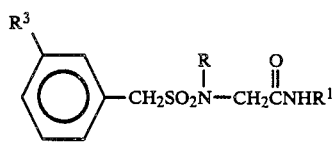

wherein R, R¹ and R³ are as defined in claim 3; and hydrates and compatible salts thereof.

13. The compound of claim 12 wherein R is methyl, ethyl, propyl, cyclopropyl, allyl, 2-propynyl, 3-iodopropargyl, methoxymethyl, 2-fluoroethyl, or 2,2,2-trifluoroethyl and R¹ is hydrogen.

14. The compound of claim 13 wherein R is ethyl, 2-propynyl, methoxymethyl, 2-fluoroethyl, or 2,2,2-trifluoroethyl.

15. The compound of claim 12 wherein R³ is trifluoromethyl or chloro and R¹ is hydrogen.

16. The compound of claim 14 wherein $R^3$ is trifluoromethyl.

17. The compound of claim 16 wherein R is ehtyl.

18. The compound of claim 15 wherein $R^3$ is chloro and $R^1$ is hydrogen.

19. The compound of claim 3 having the formula

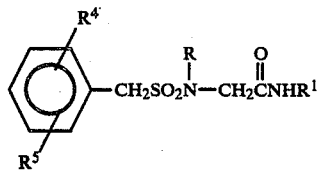

wherein
R, $R^1$, $R^4$ and $R^5$ are as defined in claim 3; and hydrates and compatible salts thereof.

20. The compound of claim 19 wherein R is methyl, ethyl, propyl, cyclopropyl, allyl, 2-propynyl, 3-iodopropargyl, methoxymethyl, 2-fluoroethyl or 2,2,2-trifluoroethyl and $R^1$ is hydrogen.

21. The compound of claim 19 wherein R is ethyl.

22. The compound of claim 19 wherein one of $R^4$ or $R^5$ is trifluoromethyl or chloro and the other is trifluoromethyl or halo.

23. The compound of claim 19 wherein $R^4$ and $R^5$ are each chloro.

24. The compound of claim 23 wherein R is methyl or ethyl and $R^1$ is hydrogen.

25. The compound of claim 3 wherein R is ethyl; $R^1$ is hydrogen and Ar is 3,5-dichlorophenyl; 2-chloro-5-trifluoromethylphenyl; or 3,5-ditrifluoromethylphenyl.

26. The compound of claim 3 wherein Ar is said trisubstituted phenyl and $R^1$ is hydrogen.

27. The compound of claim 26 wherein said trisubstituted phenyl has its three substituents independently selected from the group of chloro and trifluoromethyl.

28. The compound of claim 27 wherein R is ethyl, $R^1$ is hydrogen and said trisubstituted phenyl is 2,3-dichloro-5-trifluoromethylphenyl.

29. The compound of claim 1 wherein Ar is pentafluorophenyl.

30. The compound of claim 29 wherein R is methyl, ethyl, n-propyl, cyclopropyl, allyl, 2-propynyl, 3-iodopropargyl, methoxymethyl, 2-fluoroethyl or 2,2,2-trifluoroethyl and $R^1$ is hydrogen.

31. A compound having the formula:

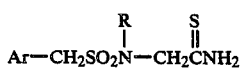

wherein
R is hydrogen, lower alkyl having 1 through 6 carbon atoms; cycloalkyl having 3 through 6 carbon atoms; (cycloalkyl)alkyl having 3 through 6 carbon atoms in the cycloalkyl moiety and 1 through 3 carbon atoms in the alkyl moiety; lower alkenyl having 2 through 6 carbon atoms; lower alkynyl having 2 through 6 carbon atoms; alkoxyalkyl wherein the alkoxy and alkyl moieties independently have 1 through 6 carbon atoms; alkylthioalkyl wherein the alkyl moieties thereof independently have 1 through 6 carbon atoms; epoxyalkylmethylene having 3 through 6 carbon atoms; haloalkylmethyl having 2 through 4 carbon atoms and 1 through 4 halo atoms independently selected from the group of fluoro, chloro and bromo; or cyanomethyl;

Ar is a substituted phenyl selected from the group of tetrafluorophenyl, pentafluorophenyl; trisubstituted phenyls having three substituents independently selected from the group of fluoro, chloro, bromo and trifluoromethyl; and substituted phenyls having the formulas

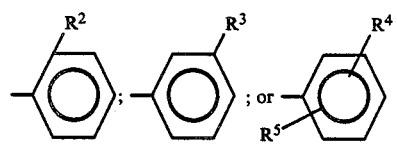

wherein $R^2$ is methyl, trifluoromethyl or chloro; $R^3$ is halo, alkyl having 1 through 4 carbon atoms, alkoxy having 1 through 4 carbon atoms, fluoroalkyl having 1 through 4 fluoro atoms and 1 through 4 carbon atoms or nitro; one of $R^4$ or $R^5$ is trifluoromethyl or chloro and the other is halo, alkyl having 1 through 4 carbon atoms, alkoxy having 1 through 4 carbon atoms, or fluoroalkyl having 1 through 4 fluoro atoms and 1 through 4 carbon atoms; and hydrates and compatible salts thereof.

32. The compound of claim 31, having the formula

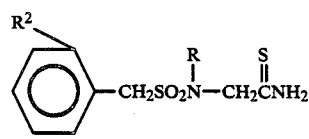

wherein R, and $R^2$ are as defined in claim 31; and hydrates and compatible salts thereof.

33. The compound of claim 32 wherein R is methyl, ethyl, propyl, cyclopropyl, allyl, 2-propynyl, 3-iodopropargyl; methoxymethyl, 2-fluoroethyl, or 2,2,2-trifluoroethyl.

34. The compound of claim 32 wherein R is methyl, ethyl, 2-propynyl, 2-fluoroethyl, or 2,2,2-trifluoroethyl.

35. The compound of claim 32 wherein $R^2$ is trifluoromethyl.

36. The compound of claim 34 wherein $R^2$ is trifluoromethyl.

37. The compound of claim 36 wherein R is ethyl.

38. The compound of claim 31 having the formula

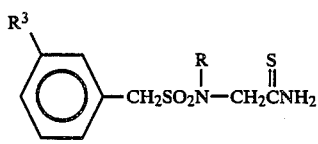

wherein R and $R^3$ are as defined in claim 31; and hydrates and compatible salts thereof.

39. The compound of claim 38 wherein R is methyl, ethyl, propyl, cyclopropyl, 2-propynyl, 3-iodopropargyl, methoxymethyl, 2-fluoroethyl, or 2,2,2-trifluoroethyl.

40. The compound of claim 39 wherein R is methyl, ethyl, 2-propynyl, methoxymethyl, 2-fluoroethyl, or 2,2,2-trifluoroethyl.

41. The compound of claim 38 wherein $R^3$ is trifluoromethyl or chloro.

42. The compound of claim 40 wherein $R^3$ is trifluoromethyl.

43. The compound of claim 42 wherein R is ethyl.

44. The compound of claim 41 wherein $R^3$ is chloro and R is ethyl.

45. The compound of claim 31 having the formula

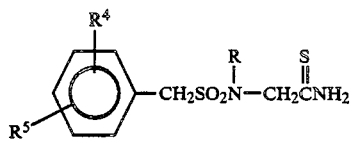

wherein R, $R^4$ and $R^5$ are as defined in claim 31; and hydrates and compatible salts thereof.

46. The compound of claim 45 wherein R is methyl, ethyl, propyl, cyclopropyl, allyl, 2-propynyl, 3-iodopropargyl, methoxymethyl, 2-fluoromethyl, or 2,2,2-trifluoroethyl and $R^1$ is hydrogen.

47. The compound of claim 45 wherein R is ethyl.

48. The compound of claim 45 wherein one of $R^4$ or $R^5$ is trifluoromethyl or chloro and the other is trifluoromethyl or halo.

49. The compound of claim 45 wherein $R^4$ and $R^5$ are each chloro.

50. The compound of claim 49 wherein R is methyl or ethyl.

51. The compound of claim 31 wherein R is ethyl, and Ar is 3,5-dichlorophenyl; 2-chloro-5-trifluoromethylphenyl or 3,5-di-trifluoromethylphenyl.

52. The compound of claim 31 wherein Ar is said trisubstituted phenyl.

53. The compound of claim 52 wherein said trisubstituted phenyl has its three substituents independently selected from the group of chloro and trifluoromethyl.

54. The compound of claim 52 wherein R is ethyl and said trisubstituted phenyl is 2,3-dichloro-5-trifluoromethylphenyl.

55. The compound of claim 31 wherein Ar is pentafluorophenyl.

56. The compound of claim 55 wherein R is methyl, ethyl, n-propyl, cyclopropyl, allyl, 2-propynyl, 3-iodopropargyl; methoxymethyl, 2-fluoromethyl, or 2,2,2-trifluoroethyl 57. A compound having the formula:

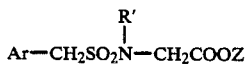

wherein

R' is hydrogen or methyl;

Ar is a substituted phenyl selected from the group of tetrafluorophenyl; pentafluorophenyl; trisubstituted phenyls having three substituents independently selected from the group of fluoro, chloro, bromo and trifluoromethyl; and substituted phenyls having the formulas

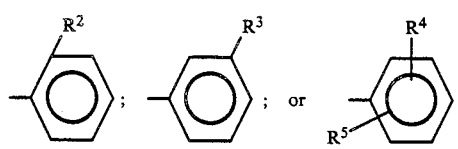

wherein $R^2$ is trifluoromethyl or chloro;

$R^3$ is halo, alkyl having 1 through 4 carbon atoms, alkoxy having 1 through 4 carbon atoms, fluoroalkyl having 1 through 4 fluoro atoms and 1 through 4 carbon atoms or nitro; one of $R^4$ or $R^5$ is trifluoromethyl or chloro and the other is halo, alkyl having 1 through 4 carbon atoms, alkoxy having 1 through 4 carbon atoms, or fluoroalkyl having 1 through 4 fluoro atoms and 1 through 4 carbon atoms; and Z is lower alkyl having 1 through 6 carbon atoms; phenyl; benzyl; or naphthyl.

58. A compound having the formula:

wherein

X is O= or S=;

R is hydrogen,

R' is hydrogen or methyl;

$R^1$ is hydrogen, alkanoyl having 2 through 5 carbon atoms, or hydroxy; with the proviso that when X is S=, then $R^1$ is hydrogen;

Ar is substituted phenyl selected from the group of tetrafluorophenyl; pentafluorophenyl; p trisubstituted phenyls having three substituents independently selected from the group of fluoro, chloro, bromo and trifluoromethyl; and substituted phenyls having the formulas

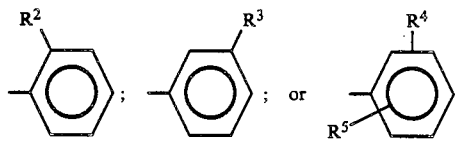

wherein $R^2$ is methyl, trifluoromethyl or chloro;

$R^3$ is halo, alkyl having 1 through 4 carbon atoms, alkoxy having 1 through 4 carbon atoms, fluoroalkyl having 1 through 4 fluoro atoms and 1 through 4 carbon atoms or nitro; one of $R^4$ or $R^5$ is trifluoromethyl or chloro and the other is halo, nitro, alkyl having 1 through 4 carbon atoms, alkoxy having 1 through 4 carbon atoms, or fluoroalkyl having 1 through 4 fluoro atoms and 1 through 4 carbon atoms; and hydrates and compatible salts of the compounds of Formula (Iy).

59. The compound of claim 57 wherein Ar is 3-chlorophenyl, 2-trifluoromethylphenyl, 3-trifluoromethylphenyl, 3,5-dichlorophenyl, 2-chloro-5-trifluoromethylphenyl, 3,5-di-trifluoromethylphenyl; or 2,3-dichloro-5-trifluoromethylphenyl.

60. A herbicidal composition comprising a herbicidally effective amount of a compound according to claim 3, or mixtures of such compounds, and a compatible carrier.

61. A herbicidal composition comprising a herbicidally effective amount of a compound according to claim 31, or mixtures thereof, and a compatible carrier.

62. A herbicidal composition comprising a herbicidally effective amount of a compound according to claim 17, or mixtures thereof, and a compatible carrier.

63. A method for controlling barnyardgrass which comprises applying a herbicidally effective amount of a compound according to claim 3, or mixtures thereof, to the foliage or habitat of said barnyardgrass.

64. A method for preventing or destroying barnyardgrass which comprises applying a herbicidally effective amount of a compound according to claim 31, or mixtures thereof, to the voliage or habitat of said barnyardgrass.

65. A method for preventing or destroying barnyardgrass which comprises applying a herbicidally effective amount of a compound according to claim 17, or mixtures thereof, to the foliage or habitat of said barnyardgrass.

66. The compound of claim 3 wherein Ar is 2-chloro-5-trifluoromethylphenyl, R is methyl and $R^1$ is hydrogen.

67. The compound of claim 3 wherein Ar is 2-chloro-5-trifluoromethylphenyl, R is ethyl and $R^1$ is hydrogen.

68. The compound of claim 3 wherein Ar is 3,5-dichlorophenyl, R is methyl and $R^1$ is hydrogen.

69. The compound of claim 3 wherein Ar is 3,5-dichlorophenyl, R is ethyl and $R^1$ is hydrogen.

70. A herbicidal composition comprising a herbicidally effective amount of a compound according to claim 67, and a compatible carrier.

71. A method for controlling barnyardgrass which comprises applying a herbicidally effective amount of a compound according to claim 67, to the foliage or habitat of said barnyardgrass.

72. A herbicidal composition comprising a herbicidally effective amount of a compound according to claim 68 and a compatible carrier.

73. A method for controlling barnyardgrass which comprises applying a herbicidally effective amount of a compound according to claim 68, to the foliage or habitat of said barnyardgrass.

74. A herbicidal composition comprising a herbicidally effective amount of a compound according to claim 69, and a compatible carrier.

75. A method for controlling barnyardgrass which comprises applying a herbicidally effective amount of a compound according to claim 69, to the foliage or habitat of said barnyardgrass.

76. A herbicidal composition comprising a herbicidally effective amount of a compound according to claim 66 and a compatible carrier.

77. A method for controlling barnyardgrass which comprises applying a herbicidally effective amount of a compound according to claim 66 to the foliage or habitat of said barnyardgrass.

78. The compound of claim 3 wherein $R^1$ is alkanoyl having 2 through 5 carbon atoms or hydroxy.

79. The compound of claim 3 wherein Ar is tetrafluorophenyl.

80. The compound of claim 31 wherein Ar is tetrafluorophenyl.

81. The compound of claim 58 wherein X is O=.

* * * * *